United States Patent [19]

Kim et al.

[11] Patent Number: 4,640,799
[45] Date of Patent: Feb. 3, 1987

[54] CARBAPENEM ANTIBIOTICS

[75] Inventors: Choung U. Kim, Manlius; Peter F. Misco, Jr., Syracuse, both of N.Y.

[73] Assignee: Bristol-Myers Company, New York, N.Y.

[21] Appl. No.: 762,735

[22] Filed: Aug. 5, 1985

Related U.S. Application Data

[60] Division of Ser. No. 499,690, Jun. 7, 1983, which is a continuation-in-part of Ser. No. 389,652, Jun. 18, 1982, abandoned.

[51] Int. Cl.$^4$ .................. C07D 487/04; A61K 31/40
[52] U.S. Cl. .................................................... 540/350
[58] Field of Search ................ 260/245.2 T, 245.2 R; 514/210

[56] References Cited

U.S. PATENT DOCUMENTS

| 4,189,493 | 2/1980 | Christensen et al. | 424/273 R |
|---|---|---|---|
| 4,218,463 | 8/1980 | Christensen et al. | 424/274 |
| 4,226,870 | 10/1980 | Christensen et al. | 424/263 |
| 4,234,596 | 11/1980 | Christensen et al. | 424/274 |
| 4,235,917 | 11/1980 | Christensen et al. | 424/274 |
| 4,235,920 | 11/1980 | Christesen et al. | 260/245.2 T |
| 4,269,772 | 5/1981 | Melillo et al. | 260/245.2 T |
| 4,273,709 | 6/1981 | Christensen et al. | 260/239 |
| 4,282,148 | 8/1981 | Liu et al. | 260/239.1 |
| 4,287,123 | 9/1981 | Liu et al. | 260/239.1 |
| 4,290,947 | 9/1981 | Christensen et al. | 260/239 R |
| 4,309,346 | 1/1982 | Christensen et al. | 260/239 |
| 4,318,912 | 3/1982 | Christensen et al. | 424/263 |
| 4,536,335 | 8/1985 | Kim et al. | 514/210 |
| 4,543,257 | 9/1985 | Cama et al. | 514/210 |

FOREIGN PATENT DOCUMENTS

| 0001627 | 5/1979 | European Pat. Off. |
| 0001628 | 5/1979 | European Pat. Off. |
| 0007973 | 2/1980 | European Pat. Off. |
| 0010317 | 4/1980 | European Pat. Off. |
| 0017992 | 10/1980 | European Pat. Off. |
| 0021082 | 1/1981 | European Pat. Off. |
| 0024832 | 3/1981 | European Pat. Off. |
| 0037080 | 10/1981 | European Pat. Off. |
| 0037081 | 10/1981 | European Pat. Off. |
| 0037082 | 10/1981 | European Pat. Off. |
| 0040408 | 11/1981 | European Pat. Off. |
| 0038869 | 11/1981 | European Pat. Off. |
| 0044170 | 1/1982 | European Pat. Off. |
| 0050334 | 4/1982 | European Pat. Off. |
| 0072710 | 2/1983 | European Pat. Off. |
| 0074599 | 3/1983 | European Pat. Off. |
| 1604276 | 12/1981 | United Kingdom |

OTHER PUBLICATIONS

Recent Advances in the Chemistry of β-Lactam Antibiotics The Royal Society of Chemistry, London, 1981 pp. 240–254.

Handout at the Gordon Research Conference on Medicinal Chemistry held at New London, New Hampshire on Aug. 2–6, 1982.

Primary Examiner—Nicholas S. Rizzo
Attorney, Agent, or Firm—David M. Morse

[57] ABSTRACT

Disclosed are novel carbapenem derivatives characterized by a 2-substituent of the formula

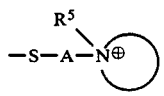

in which A represents cyclopentylene, cyclohexylene or $C_2$–$C_6$ alkylene optionally substituted by one or more $C_1$–$C_4$ alkyl groups; $R^5$ represents either (a) an optionally substituted aliphatic, cycloaliphatic, cycloaliphatic-aliphatic, aryl, aralphatic, heteroaryl, heteroaraliphatic, heterocyclyl or heterocyclyl-aliphatic radical or (b) a divalent phenylene or $C_1$–$C_4$ alkylene group joined to the

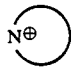

ring so as to form a bridged polycyclic group; and

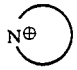

represents a quaternized nitrogen-containing non-aromatic heterocycle. Such derivatives are useful as potent antibacterial agents.

7 Claims, No Drawings

CARBAPENEM ANTIBIOTICS

This application is a division of co-pending application Ser. No. 499,690 filed June 7, 1983 which in turn is a continuation-in-part of application Ser. No. 389,652 filed June 18, 1982, now abandoned.

BACKGROUND OF THE INVENTION

1. Field of the Invention

The present invention is directed to new carbapenem antibiotics in which the 2-substituent has the formula

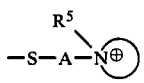

in which A represents a straight or branched chain alkylene group or a cyclopentylene or cyclohexylene group; $R^5$ represents either (a) an optionally substituted aliphatic, cycloaliphatic, cycloaliphatic-aliphatic, aryl, araliphatic, heteroaryl, heteroaraliphatic, heterocyclyl or heterocyclyl-aliphatic radical or (b) a divalent phenylene or $C_1$-$C_4$ alkylene group joined to the

ring so as to form a bridged polycyclic group; and

represents a quaternized nitrogen-containing non-aromatic heterocycle.

2. Description of the Prior Art

A number of β-lactam derivatives containing the carbapenem nucleus

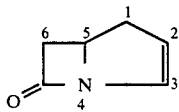

have been disclosed in the literature. These carbapenem derivatives have been reported to possess utility as antibacterial agents and/or β-lactamase inhibitors.

The initial carbapenem compounds were natural products such as thienamycin of the formula

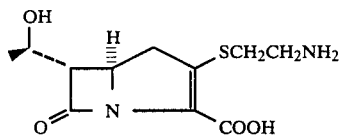

obtained by fermentation of *Streptomyces cattleya* (U.S. Pat. No. 3,950,357). Thienamycin is an exceptionally potent broadspectrum antibiotic which possesses notable activity against various Pseudomonas species, organisms which have been notoriously resistant to β-lactam antibiotics.

Other natural products containing the carbapenem nucleus include olivanic acid derivatives such as antibiotic MM 13902 of the formula

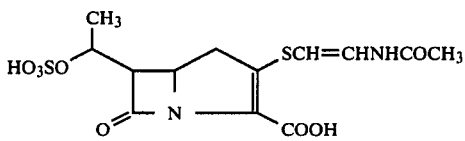

disclosed in U.S. Pat. No. 4,113,856, antibiotic MM 17880 of the formula

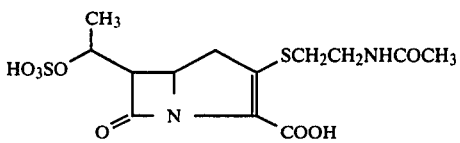

disclosed in U.S. Pat. No. 4,162,304, antibiotic MM 4550A of the formula

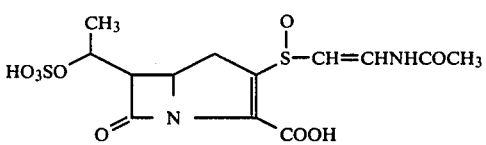

disclosed in U.S. Pat. No. 4,172,129 and antibiotic 890A$_9$ of the formula

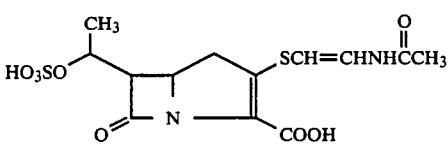

disclosed in U.S. Pat. No. 4,264,735. In addition to the natural products, the compound desacetyl 890A$_{10}$ of the formula

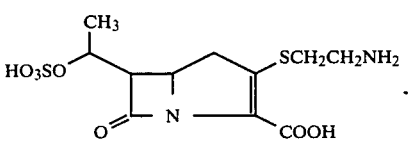

is disclosed in U.S. Pat. No. 4,264,734 as being prepared by an enzymatic deacylation of the corresponding N-acetyl compound. Various derivatives of the naturally-occuring olivanic acids have also been synthesized, e.g. the compounds of the formula

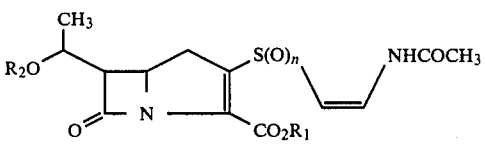

wherein $CO_2R_1$ is a free, salted or esterified carboxyl group, n is 0 or 1 and $R_2$ is H, an acyl group or a group of the formula $R_3O_3S$ wherein $R_3$ is a salting ion or a methyl or ethyl group, disclosed in European Patent Application No. 8885.

U.S. Pat. No. 4,235,922 (see also European Patent Application No. 2058) discloses the carbapenem derivative of the formula

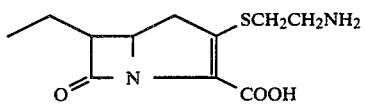

while U.K. Patent Application No. 1,598,062 reports isolation of the compound

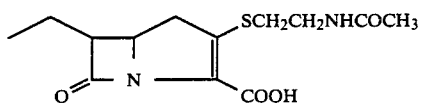

from a Streptomyces fermentation broth.

Carbapenems which are unsubstituted in the 6-position have also been synthesized. Thus, U.S. Pat. No. 4,210,661 discloses compounds of the formula

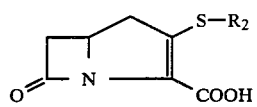

wherein $R_2$ is phenyl or substituted phenyl, U.S. Pat. No. 4,267,177 discloses compounds of the formula

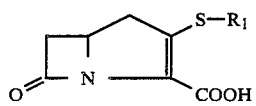

wherein $R_1$ is an optionally substituted pyridyl group, U.S. Pat. No. 4,255,441 discloses compounds of the formula

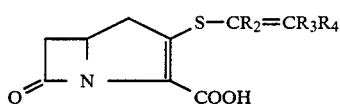

wherein $R_2$ and $R_3$ are H or alkyl and $R_4$ is NH—CO$_n$R$_6$ in which $R_6$ is alkyl, phenyl or substituted phenyl and n is 1 or 2, and U.S. Pat. No. 4,282,236 discloses compounds of the formula

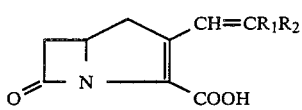

wherein $R_1$ is H or alkyl and $R_2$ is CN or CO$_2$R$_3$ in which $R_3$ is H, alkyl, aryl or aralkyl.

Carbapenems of the general formula

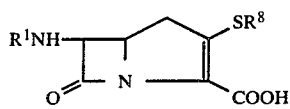

wherein $R^1$ is H or acyl and $R^8$ is H or substituted or unsubstituted: alkyl, alkenyl, alkynyl, cycloalkyl, cycloalkylalkyl, alkylcycloalkyl, aryl, aralkyl, aralkenyl, aralkynyl, heteroaryl, heteroaralkyl, heterocyclyl or heterocyclylalkyl, are disclosed in U.S. Pat. No. 4,218,463. There is no disclosure of any heterocyclylalkyl $R^8$ substituents of the type

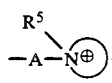

in which A is alkylene and

is a quaternized nitrogen-containing non-aromatic heterocycle.

The natural product thienamycin has the absolute configuration 5R, 6S, 8R. This isomer, as well as the remaining seven thienamycin isomers, may be obtained via total synthesis as disclosed in U.S. Pat. No. 4,234,596. Total synthesis procedures for thienamycin are also disclosed, for example, in U.S. Pat. Nos. 4,287,123, 4,269,772, 4,282,148, 4,273,709, 4,290,947 and European Patent Application No. 7973. A key intermediate in the disclosed synthetic methods is

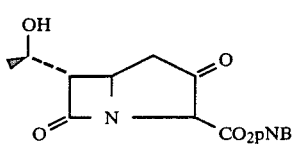

wherein pNB represents p-nitrobenzyl.

Because of the exceptional biological activity of thienamycin, a large number of derivatives have been prepared and disclosed in the literature. Among these are (1) N-formimidoyl thienamycin of the formula

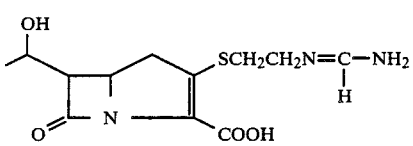

disclosed in European Patent Application No. 6639; (2) N-heterocyclic derivatives of thienamycin having the formula

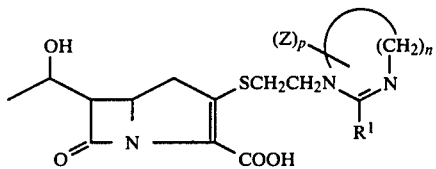

and

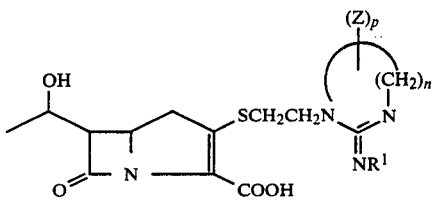

wherein: the bifunctional ring may contain additional unsaturation in the ring; and wherein n is an integer selected from 1–6; p is 0, 1 or 2; $R^1$ is H, alkyl or aryl; and Z is imino, oxo, H, amino or alkyl, disclosed in U.S. Pat. No. 4,189,493; (3) substituted N-methylene derivatives of thienamycin having the formula

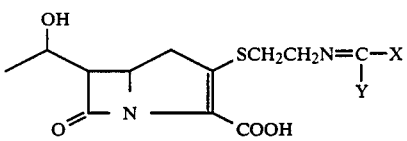

wherein X and Y are H, R, OR, SR or $NR^1R^2$ in which R is substituted or unsubstituted: alkyl, alkenyl, alkynyl, cycloalkyl, cycloalkylalkyl, aryl, aralkyl, heteroaryl, heteroaralkyl, heterocyclyl or heterocyclyalkyl, and $R^1$ and $R^2$ are H or R, disclosed in U.S. Pat. No. 4,194,047; (4) compounds of the formula

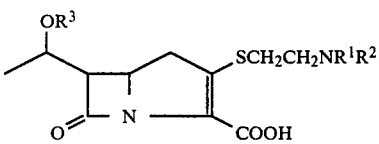

wherein $R^3$ is aryl, alkyl, acyl or aralkyl and $R^1$ and $R^2$ are independently selected from H and acyl (including acyl of the type

—C—$R^{11}$ in which $R^{11}$ may inter alia be alkyl substituted by a quaternary ammonium group, e.g.

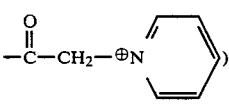

disclosed in U.S. Pat. No. 4,226,870; (5) compounds of the formula

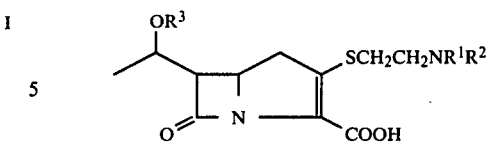

wherein $R^3$ is H, acyl or an univalent optionally substituted hydrocarbon radical; $R^1$ is optionally substituted alkyl, alkenyl, alkynyl, cycloalkyl, cycloalkenyl, cycloalkenylalkyl, cycloalkylalkyl, aryl, aralkyl, heteroaryl or heteroaralkyl and $R^2$ is acyl (including acyl of the type

—C—R in which R is alkyl substituted by a quaternary ammonium group, e.g.

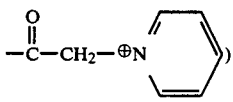

disclosed in U.K. Pat. No. 1,604,276 (see also U.S. Pat. No. 4,235,917); (6) compounds of the formula

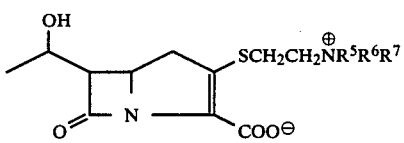

wherein $R^5$, $R^6$ and $R^7$ are independently selected from H and substituted or unsubstituted: alkyl, alkenyl, alkynyl, cycloalkyl, cycloalkenyl, cycloalkenylalkyl, cycloalkylalkyl, aryl, aralkyl, heteroaryl or heteroaralkyl, are disclosed in U.S. Pat. No. 4,235,920; (7) compounds of the formula

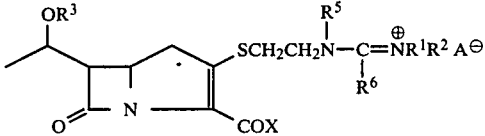

wherein each of $R^1$ and $R^2$, independently of the other, is a radical of the type defined for R, a hydrogen atom, or a nitro, hydroxyl, $C_{1-6}$ alkoxyl, amino, $C_{1-6}$ alkylamino, di($C_{1-6}$ alkyl)amino or tri($C_{1-6}$ alkylamino) radical, an extra anion being present in the latter case; or $R^1$ and $R^2$ are joined together to form, together with the nitrogen atom to which they are attached, a substituted or unsubstituted monocyclic or bicyclic heteroaryl or heterocyclyl residue containing 4–10 ring atoms, one or more of which may be an additional hetero atom selected from oxygen, sulphur and nitrogen; R is a cyano group or a substituted or unsubstituted carbamoyl, carboxyl, ($C_{1-10}$ alkoxy)carbonyl, $C_{1-10}$ alkyl, $C_{2-10}$ alkenyl, $C_{2-10}$ alkynyl, $C_{3-10}$ cycloalkyl, $C_{4-12}$ cycloalkylalkyl, $C_{5-12}$ cycloalkylalkenyl, $C_{3-10}$ cycloalkenyl, $C_{5-12}$ cycloalkenylalkyl, $C_{4-12}$ cycloalkenylalkyl, $C_{6-10}$ aryl, $C_{7-16}$ aralkyl, $C_{8-16}$ aralkenyl, $C_{8-16}$ aralkynyl or monocyclic or bicyclic heteroaryl, heteroaralkyl, heterocyclyl or heterocyclylalkyl comprising 4 to 10 ring atoms one or more of which is a hetero atom selected from oxygen, sulphur and nitrogen and in which the alkyl residue of the heteroaralkyl or heterocyclylalkyl radical contains from 1 to 6 carbon atoms; the substituent or substituents on R, $R^1$, $R^2$ or on the ring formed by joining $R^1$ and $R^2$ are chlorine; bromine; iodine; fluorine; azido; $C_{1-4}$ alkyl; mercapto; sulpho; phosphono; cyanothio (—SCN); nitro; cyano; amino; hydrazino; amino or hydrazino having up to three $C_{1-16}$ alkyl substituents; hydroxy; $C_{1-6}$ alkoxy; $C_{1-6}$ alkylthio; carboxyl; oxo; ($C_{1-6}$ alkoxy)carbonyl; $C_{2-10}$ acyloxy; carbamoyl; ($C_{1-4}$ alkyl)carbamoyl or di($C_{1-4}$ alkyl)carbamoyl; $R_3$ is a hydrogen atom, an acyl radical or a radical of the type defined for $R^4$; $R^4$ is $C_{1-10}$ alkyl; substituted carbonylmethyl; ($C_{1-6}$ alkoxy)—($C_{1-6}$ alkyl), ($C_{3-6}$ cycloalkoxy)—($C_{1-6}$ alkyl); $C_{2-12}$ alkanoyloxyalkyl; partially or completely halogenated $C_{1-6}$ alkyl in which the halogen(s) is/are chlorine, bromine or fluorine; aminoalkyl; $C_{2-10}$ alkenyl; $C_{2-10}$ alkynyl; acyl; $C_{3-14}$ alkoxycarbonylalkyl; $C_{4-21}$ dialkylaminoacetoxyalkyl; $C_{2-13}$ alkanoylaminoalkyl; ar-($C_{1-3}$ alkyl) in which the aryl residue contains from 6 to 10 carbon atoms; monocyclic or bicyclic heteroaralkyl or heterocyclylalkyl containing 4 to 10 ring atoms, 1 to 3 carbon atoms in the alkyl residue, and 1–4 hetero atoms selected from oxygen, sulphur and/or nitrogen; nuclear-substituted aralkyl or heteroaralkyl in which the substituent is chlorine, fluorine, bromine, iodine or $C_{1-6}$ alkyl; aryl or nuclear-substituted aryl containing 6 to 10 ring carbon atoms and in which any nuclear substituent is hydroxy, $C_{1-6}$ alkyl, chlorine, fluorine or bromine; aralkoxyalkyl; $C_{2-12}$ alkylthioalkyl; $C_{4-12}$ cycloalkylthioalkyl; ($C_{2-10}$ acylthio)—($C_{1-6}$ alkyl); or phenylalkenyl in which alkenyl has 2–6 carbon atoms; $R^5$ is substituted or unsubstituted $C_{1-10}$ alkyl; $C_{2-10}$ alkenyl or alkynyl; ring substituted and unsubstituted cycloalkyl, cycloalkenyl, cycloalkenylalkyl, and cycloalkylalkyl having 3–6 ring carbon atoms and up to 6 carbon atoms in any chain; $C_{6-10}$ aryl; aralkyl having 6–10 ring carbon atoms and 1–6 carbon atoms in the alkyl chain; monocyclic or bicyclic heteroaryl or heteroaralkyl containing 4–10 ring atoms, one or more of which is oxygen, nitrogen or sulphur, and 1–6 carbon atoms in the alkyl chain; and the ring or chain substituent(s) is/are chlorine, bromine, iodine, fluorine, azido, cyano, amino, $C_{1-6}$ alkylamino, di($C_{1-6}$ alkyl)amino or tri($C_{1-6}$ alkylamino) radical, an extra anion being present in the latter case, hydroxy, $C_{1-6}$ alkoxy, $C_{1-6}$ alkylthioalkyl; carboxyl; oxo, ($C_{1-6}$ alkoxy)carbonyl; $C_{2-10}$ acyloxy; carbamoyl; ($C_{1-4}$ alkyl)carbamoyl; di($C_{1-4}$ alkyl)carbamoyl; cyanothio (—SCN) or nitro; $R^6$ is hydrogen, hydroxy, mercapto, R, —OR, —SR or $NR^1R^2$, where R, $R^1$ and $R^2$ are as defined above;

X is hydroxy, mercapto, amino, acyloxy —$OR^4$, —$SR^4$, —$NHR^4$,

—OM, OQ or, when the compound is in zwitterionic form, —O⁻, in which case A⁻ is absent;
A, when the compound is not in zwitterionic form, is a counter ion;
M is a pharmaceutically acceptable cation; and Q is a blocking group as herein defined, are disclosed in U.K. Pat. No. 1,604,275; and (8) compounds of the formula

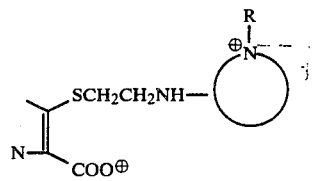

wherein

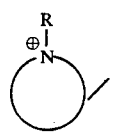

attached to the amino nitrogen group of thienamycin represents a mono- or polycyclic N-containing heterocyclic group and R is H, substituted or unsubstituted: alkyl, aryl, alkenyl, heterocyclylalkenyl, aralkenyl, heterocyclylalkyl, aralkyl, —NR₂, COOR, CONR₂, —OR, or CN, are disclosed in European Patent Application No. 21082. Among the compounds disclosed in U.S. Pat. No. 4,235,920 is

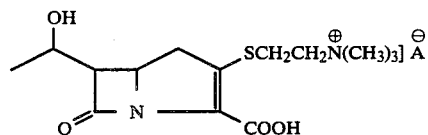

wherein A is a pharmaceutically acceptable anion. The abovementioned quaternary amine derivative is also described in *Recent Advances in the Chemistry of β-Lactam Antibiotics*, Royal Society of Chemistry, London, 1981, pg 240–254, where its antibacterial activity on average is reported as approximately ½ to ⅔ that of thienamycin.

Carbapenem derivatives having a wide variety of 6-substituents in addition to those mentioned above have also been synthesized. Thus, for example, (1) European Patent Application No. 40408 discloses compounds of the formula

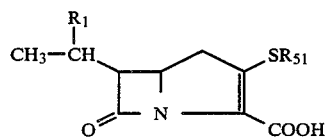

wherein $R_1$ is H, methyl or hydroxyl and $R_{51}$ is a monovalent organic group including inter alia heterocyclicmethyl; (2) European Patent Application No. 8514 discloses compounds of the formula

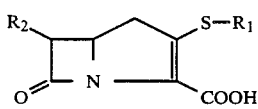

wherein $R_1$ is an optionally substituted pyrimidinyl group and $R_2$ is hydrogen or a group $CR_3R_4R_5$ wherein $R_3$ is hydrogen or hydroxy, $R_4$ is hydrogen or alkyl and $R_5$ is hydrogen, alkyl, benzyl or phenyl, or $R_5$ and $R_4$ together form a carbocyclic ring; (3) European Patent Application No. 38869 discloses compounds of the formula

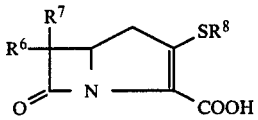

wherein $R^6$, $R^7$, and $R^8$ are independently selected from the group consisting of hydrogen, substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl; wherein the substituent or substituents relative to the above-named radicals are selected from the group consisting of:

—X° halo (chloro, bromo, fluoro)
—OH hydroxy
—OR¹ alkoxy, aryloxy $$-\overset{O}{\underset{\|}{O}}CNR^1R^2 \text{ carbamoyloxy}$$

$$-\overset{O}{\underset{\|}{C}}NR^1R^2 \text{ carbamoyl}$$

—NR¹R² amino $$-\overset{NR^1}{\underset{NR^1R^2}{\diagdown}} \text{ amidino}$$

$$\overset{R^1}{-NO_2} \text{ nitro}$$

—N(R¹)₃⁺ tri-substituted amino (R¹ group independently chosen)

$$-\overset{R^1}{\underset{|}{C}}=NOR^2 \text{ oximino}$$

—SR¹ alkyl- and arylthio
—SO₂NR¹R² sulfonamido $$-\overset{O}{\underset{\|}{NHCNR^1R^2}} \text{ ureido}$$

$$R^1\overset{O}{\underset{\|}{C}}NR^2- \text{ amido}$$

—CO₂H carboxy
—CO₂R¹ carboxylate $$-\overset{O}{\underset{\|}{CR^1}} \text{ acyl}$$

$$-\overset{O}{\underset{\|}{OCR^1}} \text{ acyloxy}$$

—SH mercapto $$-\overset{O}{\underset{\|}{SR^1}} \text{ alkyl and aryl sulfinyl}$$

$$-\overset{O}{\underset{\underset{O}{\|}}{\overset{\|}{S}R^1}} \text{ alkyl and aryl sulfonyl}$$

—CN cyano
—N₃ azido wherein, relative to the above listed substituents on $R^6$, $R^7$, and $R^8$, the groups $R^1$ and $R^2$ are independently selected from: hydrogen, alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl and wherein the hetero atom or atoms in the above-named heterocyclic moieties are selected from the group consisting of 1-4 oxygen, nitrogen or sulphur atoms and wherein the alkyl moieties associated with said heterocyclic moieties have 1-6 carbon atoms. (See also European Patent Applications Nos. 1627, 1628, 10317, 17992, 37080, 37081, and 37082); (4) European Patent Application No. 24832 discloses compounds of the formula

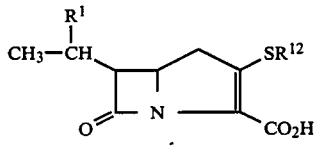

wherein $R^1$ is H or a group selected from OH, OSO₃H or a salt or C₁₋₄ alkyl ester thereof, OR², SR³, OCOR², OCO₂R³ or OCONHR³, where R² is a C₁₋₆ alkyl group or an optionally substituted benzyl group and R³ is a C₁₋₆ alkyl group or an optionally substituted benzyl or phenyl group and R¹² is C₁₋₆ alkyl, C₂₋₆ alkenyl, C₃₋₆ alkynyl wherein the triple bond is not present on the carbon adjacent to the sulfur atom, aralkyl, C₁₋₆ alkanoyl, aralkanoyl, aryloxyalkanoyl or arylcarbonyl, any of such R¹² groups being optionally substituted, as antibacterial agents.

European Patent Application No. 44170 discloses carbapenem derivatives of the formula

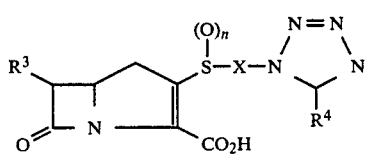

wherein R³ is hydrogen or an organic group bonded via a carbon atom to the carbapenem ring, n is 0 or 1, X is a saturated or unsaturated hydrocarbon radical optionally substituted by bromo or chloro, and R⁴ is a C₁₋₆ alkyl, C₂-C₆ alkenyl, C₁-C₁₀ aralkyl or aryl group, any of such groups R⁴ being optionally substituted. There is no disclosure, however, of any compounds wherein the tetrazole ring is bonded to X via a quaternized nitrogen atom, i.e. a positively charged nitrogen which is not attached to a hydrogen atom.

European Patent Application No. 38,869 mentioned above discloses synthesis of the carbapenem derivatives via intermediates of the general formula

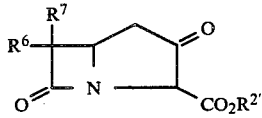

wherein $R^6$ and $R^7$ are as defined above and $R_2'$ is a readily removable carboxyl protecting group. Also disclosed as intermediates are compounds of the formula

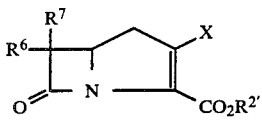

wherein X is described as a leaving group.

While, as indicated above, the prior art has described carbapenem derivatives having a 2-substituent of the general formula

wherein A represents an alkylene group and Het represents a heterocyclic or heteroaromatic group, there has been no disclosure of which applicants are aware teaching carbapenems wherein Het is a radical of the formula

in which $R^5$ is either (a) an optionally substituted aliphatic, cycloaliphatic, cycloaliphatic-aliphatic, aryl, araliphatic, heteroaryl, heteroaraliphatic, heterocyclyl or heterocyclylaliphatic radical or (b) a divalent phenylene or $C_1-C_4$ alkylene group joined to the

ring so as to form a bridged polycyclic group, and

represents a quaternized nitrogen-containing non-aromatic heterocycle bonded to the alkylene carbon via the quaternary nitrogen atom. As mentioned above, the carbapenem having

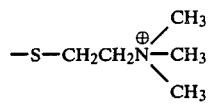

as the 2-substituent has also been reported.

Despite the vast number of carbapenem derivatives disclosed in the literature, there is still a need for new carbapenems since known derivatives may be improved upon in terms of spectrum of activity, potency, stability and/or toxic side effects.

SUMMARY OF THE INVENTION

The present invention provides a novel series of carbapenem derivatives characterized by a 2-substituent of the formula

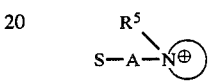

in which A represents a straight or branched chain alkylene group or a cyclopentylene or cyclohexylene group; $R^5$ represents either (a) an optionally substituted aliphatic, cycloaliphatic, cycloaliphatic-aliphatic, aryl, araliphatic, heteroaryl, heteroaraliphatic, heterocyclyl or heterocyclyl-aliphatic radical or (b) a divalent phenylene or $C_1-C_4$ alkylene group joined to the

ring so as to form a bridged polycyclic group; and

represents a quaternized nitrogen-containing non-aromatic heterocycle. Most specifically, the present invention provides carbapenem derivatives of the formula

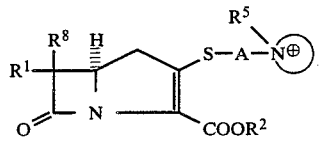

I wherein $R^8$ is hydrogen and $R^1$ is selected from the group consisting of hydrogen; substituted and unsubstituted: alkyl, alkenyl and alkynyl, having from 1–10 carbon atoms; cycloalkyl and cycloalkylalkyl, having 3–6 carbon atoms in the cycloalkyl ring and 1–6 carbon atoms in the alkyl moieties; phenyl; aralkyl, aralkenyl and aralkynyl wherein the aryl moiety is phenyl and the aliphatic portion has 1–6 carbon atoms; heteroaryl, heteroaralkyl, heterocyclyl and heterocyclylalkyl wherein the hetero atom or atoms in the above-named heterocyclic moieties are selected from the group consisting of 1–4 oxygen, nitrogen or sulfur atoms and the alkyl moieties associated with said heterocyclic moieties have 1–6 carbon atoms; wherein the substituent or substituents relative to the above-named radicals are independently selected from the group consisting of $C_1$–$C_6$ alkyl optionally substituted by amino, halo, hydroxy or carboxyl halo

—OR$^3$

—OCNR$^3$R$^4$

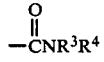
—CNR$^3$R$^4$

—NR$^3$R$^4$—

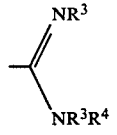

—SO$_2$NR$^3$R$^4$

—NHCNR$^3$R$^4$

R$^3$CNR$^4$

—CO$_2$R$^3$

=O $$\overset{O}{\underset{\|}{-OCR^3}}$$

—SR$^3$

—SR$^9$

—SR$^9$

—CN

—N$_3$

—OSO$_3$R$^3$

—OSO$_2$R$^3$

—NR$^3$SO$_2$R$^4$

—NR$^3$C=NR$^4$
      |
      R$^3$

—NR$^3$CO$_2$R$^4$

—NO$_2$ wherein, relative to the above-named substituents, the groups R$^3$ and R$^4$ are independently selected from hydrogen; alkyl, alkenyl and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; phenyl; aralkyl, aralkenyl and aralkynyl wherein the aryl moiety is phenyl and the aliphatic portion has 1–6 carbon atoms; and heteroaryl, heteroaralkyl, heterocyclyl and heterocyclylalkyl wherein the hetero atom or atoms in the above-named heterocyclic moieties are selected from the group consisting of 1–4 oxygen, nitrogen or sulfur atoms and the alkyl moieties associated with said heterocyclic moieties have 1–6 carbon atoms, or R$^3$ and R$^4$ taken together with the nitrogen to which at least one is attached may form a 5- or 6-membered nitrogen-containing heterocyclic ring; R$^9$ is as defined for R$^3$ except that it may not be hydrogen; or wherein R$^1$ and R$^8$ taken together represent $C_2$–$C_{10}$ alkylidene or $C_2$–$C_{10}$ alkylidene substituted by hydroxy; R$^5$ is selected from the group consisting of substituted and unsubstituted: alkyl, alkenyl and alkynyl, having from 1–10 carbon atoms; cycloalkyl and cycloalkylalkyl, having 3–6 carbon atoms in the cycloalkyl ring and 1–6 carbon atoms in the alkyl moieties; phenyl; aralkyl, aralkenyl and aralkynyl wherein the aryl moiety is phenyl and the aliphatic portion has 1–6 carbon atoms; heteroaryl, heteroaralkyl, heterocyclyl and heterocyclylalkyl wherein the hetero atom or atoms in the above-named heterocyclic moieties are selected from the group consisting of 1–4 oxygen, nitrogen or sulfur atoms and the alkyl moieties associated with said heterocyclic moieties have 1–6 carbon atoms; wherein the above-named R$^5$ radicals are optionally substituted by 1–3 substituents independently selected from:

$C_1$–$C_6$ alkyl optionally substituted by amino, fluoro, chloro, carboxyl, hydroxy or carbamoyl; fluoro, chloro or bromo;

—OR$^3$;

—OCO$_2$R$^3$;

—OCOR$^3$;

—OCONR$^3$R$^4$;

—OSO$_2$R$^3$;

—oxo;

—NR$^3$R$^4$;

R$^3$CONR$^4$—;

—NR$^3$CO$_2$R$^4$;

—NR$^3$CONR$^3$R$^4$;

—NR$^3$SO$_2$R$^4$;

—SR$^3$;

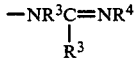

—SO$_3$R$^3$;

—CO$_2$R$^3$;

—CONR$^3$R$^4$;

—CN; or phenyl optionally substituted by 1–3 fluoro, chloro, bromo, $C_1$–$C_6$ alkyl, —OR$^3$, —NR$^3$R$^4$, —SO$_3$R$^3$, —CO$_2$R$^3$ or —CONR$^3$R$^4$, wherein R$^3$, R$^4$ and R$^9$ in such R$^5$ substituents are as defined above;

or R$^5$ may represent a divalent phenylene or $C_1$–$C_4$ alkylene group joined to the

ring so as to form a bridged polycyclic group; A is cyclopentylene, cyclohexylene or $C_2$-$C_6$ alkylene optionally substituted by one or more $C_1$-$C_4$ alkyl groups; $R^2$ is hydrogen, an anionic charge or a conventional readily removable carboxyl protecting group, providing that when $R^2$ is hydrogen or a protecting group, there is also present a counter ion; and

represents a substituted or unsubstituted mono-, bi- or polycyclic non-aromatic heterocyclic radical containing at least one nitrogen in the ring and attached to A through a ring nitrogen, thereby forming a quaternary ammonium group; or a pharmaceutically acceptable salt thereof.

The compounds of formula I are potent antibacterial agents or intermediates useful in the preparation of such agents.

Also included in the invention are processes for preparing the novel carbapenem derivatives described above and pharmaceutical compositions containing the biologically active carbapenem derivatives in combination with pharmaceutically acceptable carriers or diluents.

DETAILED DESCRIPTION

The novel compounds of general formula I above contain the carbapenem nucleus

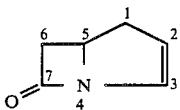

and may thus be named as 1-carba-2-penem-3-carboxylic acid derivatives. Alternatively, the compounds may be considered to have the basic structure

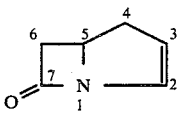

and named as 7-oxo-1-azabicyclo(3.2.0)hept-2-ene-2-carboxylic acid derivatives. While the present invention includes compounds wherein the relative stereochemistry of the 5,6-protons is cis as well as trans, the preferred compounds have the 5R,6S (trans) stereochemistry as in the case of thienamycin.

The compounds of formula I may be unsubstituted in the 6-position or substituted by substituent groups previously disclosed for other carbapenem derivatives. More specifically, $R^8$ may be hydrogen and $R^1$ may be hydrogen or a non-hydrogen substituent disclosed, for example, in European Patent Application No. 38,869 (see definition of $R_6$). Alternatively, $R^8$ and $R^1$ taken together may be $C_2$-$C_{10}$ alkylidene or $C_2$-$C_{10}$ alkylidene substituted, for example, by hydroxy.

To elaborate on the definitions for $R^1$ and $R^8$:

(a) The aliphatic "alkyl", "alkenyl" and "alkynyl" groups may be straight or branched chain having 1–10 carbon atoms; preferred are 1–6, most preferably 1–4, carbon groups; when part of another substituent, e.g. as in cycloalkylalkyl, or heteroaralkyl or aralkenyl, the alkyl, alkenyl and alkynyl group preferably contains 1–6, most preferably 1–4, carbon atoms.

(b) "heteroaryl" includes mono-, bi- and polycyclic aromatic heterocyclic groups containing 1–4 O, N or S atoms; preferred are 5- or 6-membered heterocyclic rings such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl, pyrazolyl, etc.

(c) "heterocyclyl" includes mono-, bi- and polycyclic saturated or unsaturated non-aromatic heterocyclic groups containing 1–4 O, N or S atoms; preferred are 5- or 6-membered heterocyclic rings such as morpholinyl, piperazinyl, piperidyl, pyrazolinyl, pyrazolidinyl, imidazolinyl, imidazolidinyl, pyrrolinyl, pyrrolidinyl, etc.

(d) "halo" includes chloro, bromo, fluoro and iodo and is preferably chloro, fluoro or bromo.

The term "conventional readily removable carboxyl protecting group" refers to a known ester group which has been employed to block a carboxyl group during the chemical reaction steps described below and which can be removed, if desired, by methods which do not result in any appreciable destruction of the remaining portion of the molecule, e.g by chemical or enzymatic hydrolysis, treatment with chemical reducing agents under mild conditions, irradiation with ultraviolet light or catalytic hydrogenation. Examples of such ester protecting groups include benzhydryl, allyl, p-nitrobenzyl, 2-naphthylmethyl, benzyl, trichloroethyl, silyl such as trimethylsilyl, phenacyl, p-methoxybenzyl, acetonyl, o-nitrobenzyl, 4-pyridylmethyl and $C_1$-$C_6$ alkyl such as methyl, ethyl or t-butyl. Included within such protecting groups are those which are hydrolyzed under physiological conditions such as pivaloyloxymethyl, acetoxymethyl, phthalidyl, indanyl and methoxymethyl. Particularly advantageous carboxyl protecting groups are p-nitrobenzyl which may be readily removed by catalytic hydrogenolysis and allyl which can be removed by $Pd(P\phi_3)_4$-catalyzed reaction.

The pharmaceutically acceptable salts referred to above include the nontoxic acid addition salts, e.g. salts with mineral acids such as hydrochloric, hydrobromic, hydroiodic, phosphoric, sulfuric, etc. and salts with organic acids such as maleic, acetic, citric, succinic, benzoic, tartaric, fumaric, mandelic, ascorbic, lactic, gluconic and malic. Compounds of formula I in the form of acid addition salts may be written as

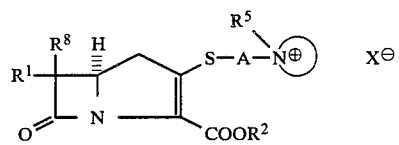

$R^2$ = H or protecting group where $X^\ominus$ represents the acid anion. The counter anion $X^\ominus$ may be selected so as to provide pharmaceutically acceptable salts for therapeutic administration but, in the case of intermediate compounds of formula I, $X^{\ominus}$ may also be a toxic anion. In such a case the ion can be subsequently removed or substituted by a pharmaceutically acceptable anion to form an active end product for therapeutic use. When acidic or basic groups are present in the $R^1$ or $R^5$ group or on the

radical, the present invention may also include suitable base or acid salts of these functional groups, e.g. acid addition salts in the case of a basic group and metal salts (e.g. sodium, potassium, calcium and aluminum), the ammonium salt and salts with nontoxic amines (e.g. trialkylamines, procaine, dibenzylamine, 1-ephenamine, N-benzyl-β-phenethylamine, N,N'-dibenzylethylenediamine, etc.) in the case of an acidic group.

Compounds of formula I wherein $R^2$ is hydrogen, an anionic charge or a physiologically hydrolyzable ester group together with pharmaceutically acceptable salts thereof are useful as antibacterial agents. The remaining compounds of formula I are valuable intermediates which can be converted into the abovementioned biologically active compounds.

A preferred embodiment of the present invention comprises compounds of formula I wherein $R^8$ is hydrogen and $R^1$ is hydrogen, $CH_3CH_2$—

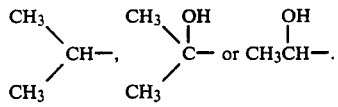

Among this subclass, the preferred compounds are those in which $R^1$ is

most preferably compounds having the absolute configuration 5R, 6S, 8R.

Another preferred embodiment comprises compounds of formula I in which $R^1$ and $R^8$ taken together form an alkylidene radical of the formula

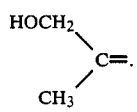

The alkylene or cycloalkylene substituent A in the compounds of formula I may be $C_2$-$C_6$ alkylene (straight chain) optionally substituted by one or more (preferably 1 or 2) $C_1$-$C_4$ alkyl groups or it may be cyclopentylene or cyclohexylene. The alkylene A substituent is preferably straight or branched chain alkylene of from 2 to 6 carbon atoms. A cycloalkylene A substituent is preferably cyclopentylene of the formula

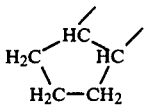

or cyclohexylene of the formula

A preferred embodiment comprises those compounds in which A is

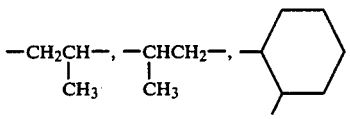

or —$(CH_2)_n$— in which n is 2, 3 or 4 and a particularly preferred embodiment comprises those compounds where A is —$CH_2CH_2$—, —$CH_2CH_2CH_2$—,

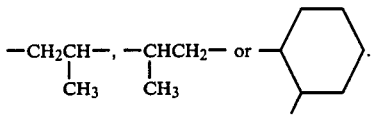

The alkylene or cycloalkylene moiety "A" is attached to an N-substituted quaternized non-aromatic heterocycle of the general formula

wherein the $R^5$ substituent may be either (a) an optionally substituted $C_1$-$C_6$ alkyl, $C_2$-$C_{10}$ alkenyl, $C_2$-$C_{10}$ alkynyl, $C_3$-$C_6$ cycloalkyl, $C_3$-$C_6$ cycloalkyl-$C_1$-$C_6$ alkyl, phenyl, phenyl-$C_1$-$C_6$ alkyl, phenyl-$C_2$-$C_6$ alkenyl, phenyl-$C_2$-$C_6$ alknynyl, heteroaryl, heteroaralkyl in which the alkyl moiety has 1-6 carbon atoms, heterocyclyl or heterocyclylalkyl in which the alkyl moiety has 1-6 carbon atoms or (b) a divalent phenylene or $C_1$-$C_4$ alkylene group joined to the

ring so as to form a bridged ring polycyclic group, e.g. a quinuclidine group. The heteroaryl (or heteroaryl portion of heteroaralkyl) substituent may be a mono-, bi- or polycyclic aromatic heterocyclic group containing 1–4 O, N or S atoms; preferred are 5- or 6-membered heterocyclic rings such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl and pyrazolyl. The heterocyclyl (or heterocyclyl portion of heterocyclylalkyl) substituent may be a mono-, bi- or polycyclic saturated or unsaturated non-aromatic heterocyclic group containing 1-4 O, N or S atoms; preferred are 5- or 6-membered heterocyclic rings such as morpholinyl, piperazinyl, piperidyl, pyrazolinyl, pyrazolidinyl, imidazolinyl, imidazolidinyl, pyrrolinyl and pyrrolidinyl.

In the case where the $R^5$ substituent is an alkyl, alkenyl, alkynyl, cycloalkyl, cycloalkylalkyl, phenyl, phenylalkyl, phenylalkenyl, phenylalkynyl, heteroaryl, heteroaralkyl, heterocyclyl or heterocyclylalkyl group, such groups may be optionally substituted by 1-3 substituents independently selected from:

(a) $C_1-C_6$ alkyl optionally substituted by, preferably 1-3, amino, fluoro, chloro, carboxyl, hydroxy or carbamoyl groups;
(b) fluoro, chloro or bromo;
(c) —$OR^3$;
(d) —$OCO_2R^3$;
(e) —$OCOR^3$;
(f) —$OCONR^3R^4$;
(g) —$OSO_2R^3$;
(h) —oxo;
(i) —$NR^3R^4$;
(j) $R^3CONR^4$—;
(k) —$NR^3CO_2R^4$;
(l) —$NR^3CONR^3R^4$;
(m) —$NR^3SO_2R^4$;
(n) —$SR^3$;
(o) —$SOR^9$;
(p) —$SO_2R^9$;
(q) —$SO_3R^3$;
(r) —$CO_2R^3$;
(s) —$CONR^3R^4$;
(t) —CN; or
(u) phenyl optionally substituted by 1-3 substituents independently selected from fluoro, chloro, bromo, $C_1-C_6$ alkyl, —$OR^3$, —$NR^3R^4$, —$SO_3R^3$, —$CO_2R^3$ or —$CONR^3R^4$, wherein, relative to the above-named $R^5$ substituents, the groups $R^3$ and $R^4$ are independently selected from hydrogen; alkyl, alkenyl and alkynyl, having 1-10 carbon atoms; cycloalkyl, cycloalkylalkyl and alkylcycloalkyl, having 3-6 carbon atoms in the cycloalkyl ring and 1-6 carbon atoms in the alkyl moieties; phenyl; aralkyl, aralkenyl and aralkynyl wherein the aryl moiety is phenyl and the aliphatic portion has 1-6 carbon atoms; and heteroaryl, heteroaralkyl, heterocyclyl and heterocyclylalkyl wherein the heteroaryl and heterocyclyl group or portion of a group is as defined above for $R^5$ and the alkyl moieties associated with said heterocyclic moieties have 1-6 carbon atoms; or $R^3$ and $R^4$ taken together with the nitrogen to which at least one is attached may form a 5- or 6-membered nitrogen-containing heterocyclic (as defined above for $R^5$) ring; and $R^9$ is as defined above for $R^3$ except that it may not be hydrogen. A most preferred $R^5$ substituent is $C_1-C_6$ alkyl, especially methyl.

In the case where $R^5$ is a divalent phenylene or $C_1-C_6$ alkylene group, such group is bonded to another atom of the

ring so as to form a bridged polycyclic ring, e.g. a quaternized quinuclidine ring of the formula

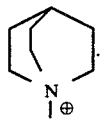

The

substituent of formula I represents an optionally substituted non-aromatic (which may be fused to another aromatic or non-aromatic ring) mono-, bi- or polycyclic nitrogen-containing heterocyclic radical attached to substitutent A through a ring nitrogen atom, thereby forming a quaternary ammonium group. The heterocyclic radical may be saturated or unsaturated (with 1-2 double bonds) and may contain up to two additional hetero atoms in addition to the quaternary nitrogen, such additional hetero atoms being selected from O, $S(O)_m$, N, $NR^{10}$ or $NR^{15}R^{16}$ wherein m is 0, 1 or 2, $R^{10}$ is hydrogen, optionally substituted $C_1-C_6$ alkyl or optionally substituted phenyl and $R^{15}$ and $R^{16}$ are each independently optionally substituted $C_1-C_6$ alkyl or optionally substituted phenyl.

In a preferred embodiment

represents a non-aromatic 4-7 membered, preferably 5- or 6-membered, N-containing heterocyclic ring containing 0-2 double bonds and 0-2 additional heteroatoms selected from O, $S(O)_m$, N, $NR^{10}$ or $NR^{15}R^{16}$ wherein m is 0, 1 or 2, $R^{10}$ is hydrogen, $C_1-C_6$ alkyl optionally substituted by 1-2 substituents independently selected from —$OR^3$, —$NR^3R^4$, —$CO_2R^3$, oxo, phenyl, fluoro, chloro, bromo, —$SO_3R^3$ and —$CONR^3R^4$ or phenyl optionally substituted by 1-3 substituents independently selected from $C_1-C_6$ alkyl, —$OR^3$, —$NR^3R^4$, fluoro, chloro, bromo, —$SO_3R^3$, —$CO_2R^2$ and —$CONR^3R^4$, and $R^{15}$ and $R^{16}$ are each independently $C_1-C_6$ alkyl optionally substituted by 1-2 substituents independently selected from —$OR^3$, —$NR^3R^4$, —$CO_2R^3$, oxo, phenyl, fluoro, chloro, bromo, —$SO_3R^3$ and —$CONR^3R^4$ or phenyl optionally substituted by 1-3 substituents independently selected from $C_1-C_6$ alkyl, —$OR^3$, —$NR^3R^4$, fluoro, chloro, bromo, —$SO_3R^3$, —$CO_2R^2$ and —$CONR^3R^4$, wherein $R^3$ and $R^4$ in such heterocyclic $NR^{10}$ and $NR^{15}R^{16}$ groups are as defined in connection with the R[5] substituent. In such preferred embodiment the

ring may be optionally substituted by 1–3 substituents independently selected from
(a) $C_1$–$C_6$ alkyl optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$;
(b) $C_2$–$C_6$ alkenyl optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$;
(c) $C_2$–$C_6$ alkynyl optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$;
(d) $C_3$–$C_6$ cycloalkyl optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$;
(e) cycloalkylalkyl having 3–6 carbon atoms in the cycloalkyl ring and 1–6 carbon atoms in the alkyl moiety, optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$;
(f) heteroaryl wherein the hetero atom or atoms are selected from the group consisting of 1–4 oxygen, nitrogen or sulfur atoms, optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$; preferred heteroaryl radicals are 5- or 6-membered aromatic heterocyclic rings;
(g) heteroaralkyl wherein the hetero atom or atoms are selected from the group consisting of 1–4 oxygen, nitrogen or sulfur atoms and the alkyl moiety has 1–6 carbon atoms, optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$; preferred heteroaralkyl are those in which the heteroaryl radical is a 5- or 6-membered aromatic heterocyclic ring and the alkyl moiety has 1–2 carbon atoms;
(h) heterocyclyl wherein the hetero atom or atoms are selected from the group consisting of 1–4 oxygen, nitrogen or sulfur atoms, optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$; preferred heterocyclyl are 5- or 6-membered saturated or unsaturated rings;
(i) heterocyclylalkyl wherein the hetero atom or atoms are selected from the group consisting of 1–4 oxygen, nitrogen or sulfur atoms and the alkyl moiety has 1–6 carbon atoms, optionally substituted by 1–2 substituents independently selected from fluoro, chloro, bromo, —$OR^3$, —$OCOR^3$, —$OCONR^3R^4$, oxo, —$NR^3R^4$, —$NR^3COR^4$, —$NR^3CONR^3R^4$, —$NR^3SO_2R^4$, —$SR^3$, —$SO_3R^3$, —$CO_2R^3$ and —$CONR^3R^4$; preferred heterocyclylalkyl are those in which the heterocyclyl moiety is a 5- or 6-membered saturated or unsaturated ring;
(j) fluoro, chloro or bromo;
(k) —$OR^3$;
(l) —$OCO_2R^3$;
(m) —$OCOR^3$;
(n) —$OCONR^3R^4$;
(o) —$OSO_2R^3$;
(p) oxo;
(q) —$NR^3R^4$;
(r) $R^3CONR^4$—;
(s) —$NR^3CO_2R^4$;
(t) —$NR^3CONR^3R^4$;
(u) —$NR^3SO_2R^4$;
(v) —$SR^3$;
(w) 
(x) 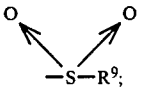
(y) —$SO_3R^3$;
(z) —$CO_2R^3$;
(aa) —$CONR^3R^4$;
(bb) —CN; or
(cc) phenyl optionally substituted by 1–3 fluoro, chloro, bromo, $C_1$–$C_6$ alkyl, —$OR^3$, —$NR^3R^4$, —$SO_3R^3$, —$CO_2R^3$ or —$CONR^3R^4$.

The $R^3$, $R^4$ and $R^9$ substituents mentioned above are as defined in connection with substituent $R^1$.

The

ring as defined above is a non-aromatic heterocyclic group. This ring, however, may be fused to another ring which may be a saturated or unsaturated carbocyclic ring, preferably a $C_4$–$C_7$ carbocyclic ring, a phenyl ring, a 4–7 membered heterocyclic (saturated or unsaturated) ring containing 1–3 hetero atoms selected from O, $S(O)_m$, N, $NR^{10}$ or $NR^{15}R^{16}$ or a 5–6 membered heteroaromatic ring containing 1–3 hetero atoms selected from O, S(O)$_m$, N, NR$^{10}$ or NR$^{15}$R$^{16}$ in which m, R$^{10}$, R$^{15}$ and R$^{16}$ are as defined above. The fused carbocyclic, phenyl, heterocyclic or heteroaromatic ring may be optionally substituted by 1-3 substituents independently selected from C$_1$-C$_6$ alkyl, —OR$^3$, —NR$^3$R$^4$, fluoro, chloro, bromo, —SO$_3$R$^3$, —CO$_2$R$^3$ and —CONR$^3$R$^4$ wherein R$^3$ and R$^4$ are as defined above.

Within the above-described preferred embodiment, the preferred compounds are those in which A is —CH$_2$CH(CH$_3$)—, —CH(CH$_3$)CH$_2$—, cyclohexyl, or —(CH$_2$)$_n$— in which n is 2, 3 or 4, most preferably those in which A is —CH$_2$CH$_2$—, —CH$_2$CH$_2$CH$_2$—, —CH$_2$CH(CH$_3$)—, —CH(CH$_3$)CH$_2$— or cyclohexyl and wherein either (a) R$^1$ and R$^8$ taken together represent

HOCH$_2$\C(CH$_3$)= or (b) R$^8$ is hydrogen and R$^1$ represents hydrogen, CH$_3$CH$_2$—, (CH$_3$)$_2$CH—, (CH$_3$)$_2$C(OH)—, or CH$_3$CH(OH)—.

Particularly preferred are the compounds wherein R$^8$ is hydrogen and R$^1$ is

CH$_3$CH(OH)—, especially compounds having the absolute configuration 5R, 6S, 8R.

A particularly preferred embodiment of the present invention comprises compounds of formula I wherein

R$^5$\N$^⊕$ represents

CH$_3$\N$^⊕$(pyrrolidine)—Y, CH$_3$\N$^⊕$(piperidine)—Y,

CH$_3$\N$^⊕$(morpholine O), CH$_3$\N$^⊕$(thiomorpholine S),

CH$_3$\N$^⊕$(piperazine NH), —$^⊕$N(quinuclidine)—Y,

CH$_3$\N$^⊕$(piperazine N—CH$_3$), CH$_3$\N$^⊕$(thiomorpholine S→O),

CH$_3$\N$^⊕$(piperazine N(CH$_3$)$_2$), CH$_3$\N$^⊕$(isoindoline),

CH$_3$\N$^⊕$(thienopyridine)

wherein Y is hydrogen, C$_1$-C$_6$ alkyl, hydroxy, —SC$_1$-C$_6$ alkyl, carboxyl, carbamoyl, chloro, bromo, iodo, fluoro or phenyl. Within this subclass, the preferred compounds are those wherein A is —CH(CH$_3$)CH$_2$—, cyclohexyl, —CH$_2$CH(CH$_3$)— or —(CH$_2$)$_n$— in which n is 2, 3 or 4, more preferably those in which A is —CH$_2$CH$_2$—, —CH$_2$CH$_2$CH$_2$—, —CH(CH$_3$)CH$_2$—, cyclohexyl or —CH$_2$CH(CH$_3$)— and most preferably those in which A is —CH$_2$CH$_2$—, and wherein either (a) R$^1$ and R$^8$ taken together represents

HOCH$_2$\C(CH$_3$)= or (b) R$^8$ is hydrogen and R$^1$ represents hydrogen, CH$_3$CH$_2$—,

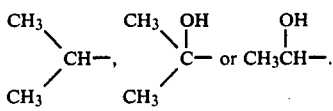

Particularly preferred are the compounds wherein $R^8$ is hydrogen and $R^1$ is

especially compounds having the absolute configuration 5R, 6S, 8R.

A still more preferred embodiment of the present invention comprises compounds of formula I wherein

represents

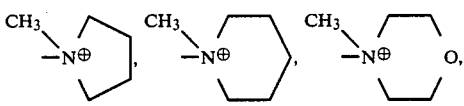

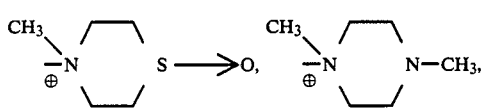

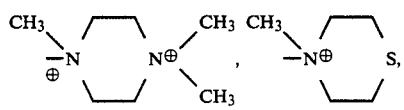

Within this preferred subclass, the preferred compounds are those wherein A is

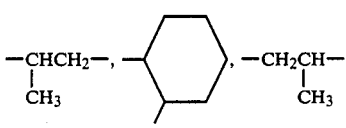

or —(CH$_2$)$_n$— in which A is 2, 3 or 4, more preferably those in which A is —CH$_2$CH$_2$—, —CH$_2$CH$_2$CH$_2$—,

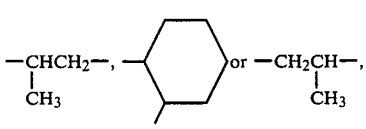

and most preferably those in which A is —CH$_2$CH$_2$—, and wherein either (a) $R^1$ and $R^8$ taken together represent

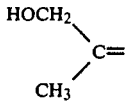

or (b) $R^8$ is hydrogen and $R^1$ represents hydrogen, CH$_3$CH$_2$—,

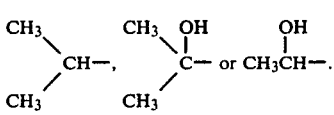

Particularly preferred are the compounds wherein $R^8$ is hydrogen and $R^1$ is

especially compounds having the absolute configuration 5R, 6S, 8R.

A still more preferred embodiment of the present invention comprises compounds of formula I wherein

represents

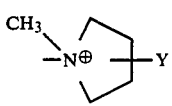

in which Y is hydrogen, C$_1$-C$_6$ alkyl, hydroxy, —S—C$_1$-C$_6$ alkyl, carboxyl, carbamoyl, chloro, bromo, iodo, fluoro or phenyl. Within this preferred subclass, the preferred compounds are those wherein A is —(CH$_2$)$_n$ in which n is 2, 3 or 4, most preferably those in which A is —CH$_2$CH$_2$— and wherein either (a) $R^1$ and $R^8$ taken together represent

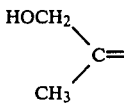

or (b) $R^8$ is hydrogen and $R^1$ represents hydrogen, CH$_3$CH$_2$—,

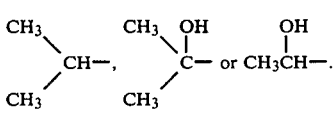

Particularly preferred are the compounds wherein $R^8$ is hydrogen and $R^1$ is

especially compounds having the absolute configuration 5R, 6S, 8R.

A most preferred embodiment of the present invention comprises compounds of formula I wherein

represents

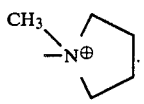

Within this preferred subclass, the preferred compounds are those wherein A is —(CH$_2$)$_n$— in which n is 2, 3 or 4, most preferably those in which A is —CH$_2$CH$_2$— and wherein either (a) R$^1$ and R$^8$ taken together represent

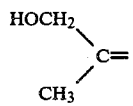

or (b) R$^8$ is hydrogen and R$^1$ represents hydrogen, CH$_3$CH$_2$—,

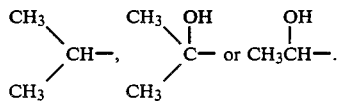

Particularly preferred are the compounds wherein R$^8$ is hydrogen and R$^1$ is

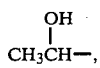

especially compounds having the absolute configuration 5R, 6S, 8R.

The most preferred embodiments of the present invention comprise the compounds of the formula

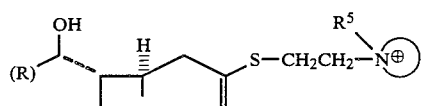

wherein 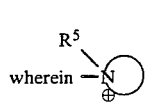 represents 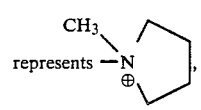

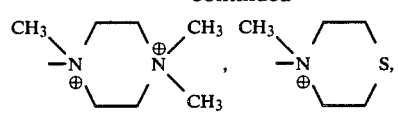

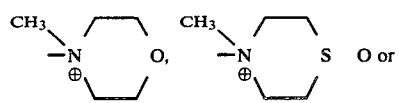

(both α- and β-diastereoisomers)

and R$^2$ is hydrogen, an anionic charge or a conventional readily removable carboxyl protecting group, providing that when R$^2$ is hydrogen or a protecting group, there is also present a counter ion, and pharmaceutically acceptable acid addition salts thereof.

It will be appreciated that certain products within the scope of formula I may be formed as optical isomers as well as epimeric mixtures thereof. It is intended that the present invention include within its scope all such optical isomers and epimeric mixtures. For example, when the 6-substituent is hydroxyethyl, such substituent may be in either the R or S configuration and the resulting isomers as well as epimeric mixtures thereof are encompassed by the present invention.

The carbapenem derivatives of general formula I are prepared from starting materials of the formula

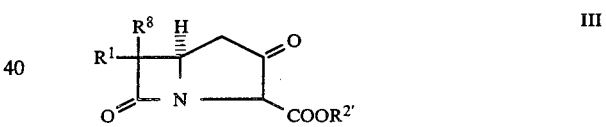

wherein R$^1$ and R$^8$ are defined above and wherein R$^{2'}$ represents a conventional readily removable carboxyl protecting group. Compounds of formula III have been disclosed, for example, in European Patent Application 38,869 (compound 7) and may be prepared by the general methods described therein.

One process for preparing compounds I from starting materials III may be summarized by the following reaction scheme:

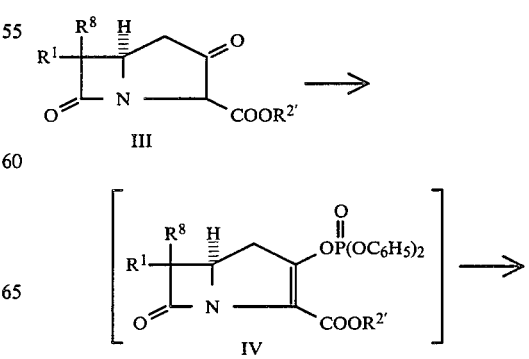

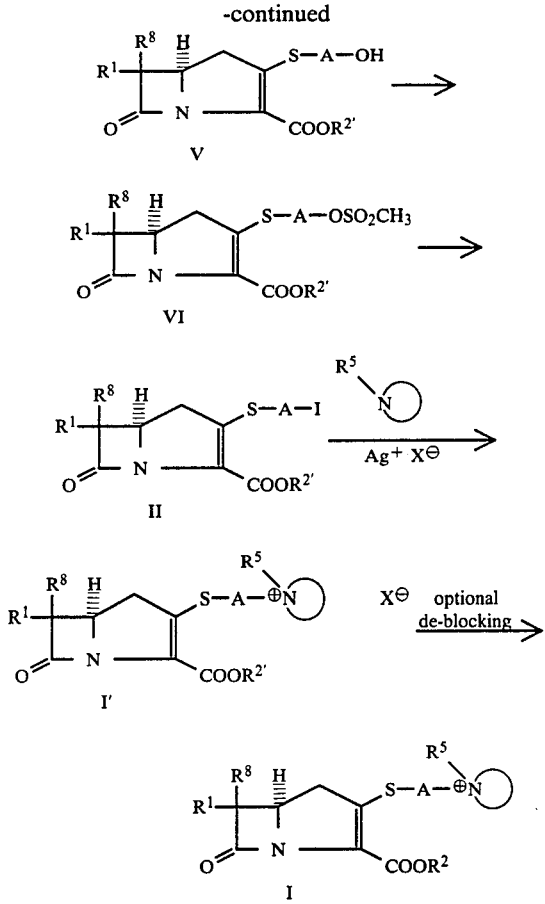

To elaborate on the above process, starting maerial III is reacted in the inert organic solvent such as methylene chloride, acetonitrile or dimethylformamide with about an equimolar amount of diphenyl chlorophosphate in the presence of a base such as diisopropylethylamine, triethylamine, 4-dimethylaminopyridine or the like to give intermediate IV. The acylation to establish the diphenylphosphoryloxy leaving group at the 2-position of intermediate III is advantageously carried out at a temperature of from about −20° to +40° C., most preferably at about 0° C. Intermediate IV may be isolated if desired, but is conveniently used for the next step without isolation or purification.

Intermediate IV is next converted to intermediate V by a conventional displacement reaction. Thus, intermediate IV may be reacted with approximately an equimolar amount of a mercaptan reagent of the formula

HS—A—OH wherein A represents cyclopentylene, cyclohexylene or $C_2$-$C_6$ alkylene optionally substituted by one or more $C_1$-$C_4$ alkyl groups in an inert organic solvent such as dioxane, dimethylformamide, dimethylsulfoxide or acetonitrile and in the presence of a base such as diisopropylethylamine, triethylamine, sodium hydrogen carbonate, potassium carbonate or 4-dimethylaminopyridine. The temperature for the displacement is not critical, but an advantageous temperature range is from about −40° C. to 25° C. Most conveniently, the reaction is carried out with cooling, e.g. at about 0° C.

Intermediate V is then acylated with methanesulfonyl chloride or a functional acylating equivalent thereof such as methanesulfonic acid anhydride in an inert organic solvent and in the presence of base to provide the methanesulfonyloxy leaving group of intermediate VI. The acylation is carried out in an inert organic solvent such as tetrahydrofuran, methylene chloride, acetonitrile or dimethylformamide and in the presence of a suitable base such as diisopropylethylamine, triethylamine, 4-dimethylaminopyridine, and the like. The reaction may be carried out over a wide temperature range, e.g. −40° C. to +40° C., but is most advantageously conducted with cooling, e.g. at about −30° C. to −40° C.

Intermediate VI is next subjected to a displacement reaction so as to provide in intermediate II the iodo leaving group. This particular group has been found to greatly facilitate preparation of the carbapenem end-products of formula I.

The displacement of the methanesulfonyloxy leaving group is carried out by reacting intermediate VI with a source of iodide ions in an inert organic solvent such as acetone, dimethylformamide or dimethylsulfoxide. Any compound which ionizes in the solvent employed to provide iodide ions may be used, e.g. an alkali metal iodide such as NaI or KI. The temperature for the displacement is not critical, but temperatures of room temperature or above are most advantageous for achieving completion of the reaction in a reasonable time period. The source of iodide ions is employed in an amount so as to provide approximately an equivalent or excess of iodide ion relative to intermediate VI.

Preparation of the desired carbapenem derivatives of formula I is carried out by a nucleophilic displacement of the iodo leaving group of intermediate II by the desired nitrogen-containing heterocyclic nucleophile

Intermediate II is reacted with at least an equivalent, preferably an excess, of the desired amine reagent in an inert organic solvent and in the presence of silver ion. Suitable inert organic solvents include, for example, tetrahydrofuran, dioxane, methylene chloride, diglyme, dimethoxyethane, and the like. Any silver compound which substantially ionizes in the solvent to give silver ions and an inert anion may be used as the source of silver ion, e.g. $AgClO_4$. Generally, we prefer to use approximately an equivalent amount (relative to intermediate II) of silver ion to facilitate the displacement. The reaction may be carried out over a wide temperature range, e.g. from about −25° to about +25° C., but is most preferably conducted at around 0° C. Intermediate I′ will have a counter anion (e.g. derived from the silver salt used) associated with it which may at this stage be substituted by a different counter anion, e.g. one which is pharmaceutically acceptable, by conventional procedures. Alternatively, the counter ion may be subsequently removed during the de-blocking step.

The de-blocking step to remove the carboxyl protecting group $R^{2'}$ of intermediate I′ is accomplished by conventional procedures such as solvolysis, chemical reduction or hydrogenation. Where a protecting group such as p-nitrobenzyl, benzyl, benzhydryl or 2-naphthylmethyl is used which can be removed by catalytic hydrogenation, intermediate I' in a suitable solvent such as dioxane-water-ethanol, tetrahydrofuran-diethylether-buffer, tetrahydrofuranaqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature of from 0° to 50° C. for from about 0.24 to 4 hours. When $R^{2'}$ is a group such as o-nitrobenzyl, photolysis may also be used for deblocking. Protecting groups such as 2,2,2-trichloroethyl may be removed by mild zinc reduction. The allyl protecting group may be removed with a catalyst comprising a mixture of a palladium compound and triphenyl phosphine in an aprotic solvent such as tetrahydrofuran, diethyl ether or methylene chloride. Similarly, other conventional carboxyl protecting groups may be removed by methods known to those skilled in the art. Finally, as mentioned above, compounds of formula I' where $R^{2'}$ is a physiologically hydrolyzable ester such as acetoxymethyl, phthalidyl, indanyl, pivaloyloxymethyl, methoxymethyl, etc. may be administered directly to the host without de-blocking since such esters are hydrolyzed in vivo under physiological conditions.

Preparation of certain compounds of general formula I may involve a further reaction step just prior to or following the de-blocking reaction. Thus, for example, when the desired heterocyclic nitrogen-containing substituent

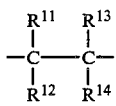

contains a sulfoxide group, one can first make the corresponding compound having the sulfur-containing heterocycle by the above process and then subject such compound, either before or after carboxyl de-blocking, to oxidation so as to form the corresponding sulfoxide end-product.

While the above-described process is suitable for preparing the compounds of the present invention, our colleague Pierre Dextraze has invented a new process which can be used to prepare compounds of formula I where substituent A is cyclopentylene, cyclohexylene or

in which $R^{11}$, $R^{12}$, $R^{13}$ and $R^{14}$ are each independently hydrogen or $C_1$-$C_4$ alkyl. This process, which is disclosed and claimed in a co-pending U.S. patent application filed even date with the present continuation-in-part application is the preferred process for preparing the above-mentioned class of compounds.

The alternative process for preparing compounds of Formula I wherein A is cyclopentylene, cyclohexylene or

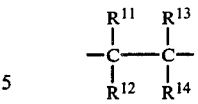

in which $R^{11}$, $R^{12}$, $R^{13}$ and $R^{14}$ are each independently hydrogen or $C_1$-$C_4$ alkyl comprises reacting an intermediate of the formula

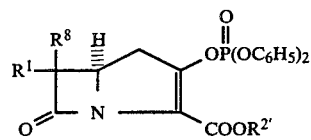

IV wherein $R^1$ and $R^8$ are as defined for the compounds of formula I and $R^{2'}$ is a conventional readily removable carboxyl protecting group with a thiol compound of the formula

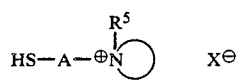

VII wherein A and

are as defined above in connection with the compounds of Formula I and $X^\ominus$ is a counter anion in an inert solvent and in the presence of base to produce the carbapenem product of the formula

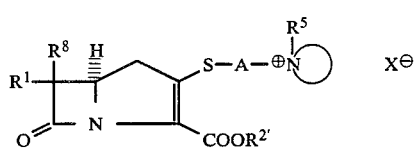

I' wherein $R^1$, $R^8$, $R^{2'}$, A,

and $X^\ominus$ are as defined above and, if desired, removing the carboxyl protecting group $R^{2'}$ to give the corresponding de-blocked compound of Formula I, or a pharmaceutically acceptable salt thereof.

The above alternative process utilizes intermediate IV which may be prepared as described above for the general synthetic process. Intermediate IV is generally prepared in situ from intermediate III and used without isolation or purification.

In the alternative process, carbapenem intermediate IV is reacted with a quaternary amine thiol of the formula

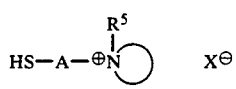 VII wherein A is cyclopentylene, cyclohexylene or

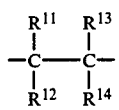

in which $R^{11}$, $R^{12}$, $R^{13}$ and $R^{14}$ are each independently hydrogen or $C_1$-$C_4$ alkyl, $X^{\ominus}$ is a counter anion associated with a strong acid such as $Cl^-$, $Br^-$, $CH_3SO_3^-$, $CF_3SO_3^-$ or

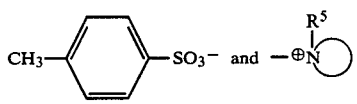

is as defined above. The reaction is carried out in an inert solvent such as acetonitrile, acetonitrile-H₂O, acetonitrile-dimethylformamide, tetrahydrofuran, tetrahydrofuran-H₂O or acetone in the presence of base. The nature of the base is not critical. Best results, however, have been obtained when a non-nucleophilic tertiary amine base such as diisopropylethylamine, 1,8-diazabicyclo[5.4.0]undec-7-ene, 1,5-diazabicyclo[4.3.0]-non-5-ene or a tri($C_1$-$C_4$)alkylamine such as triethylamine, tributylamine or tripropylamine is employed. Reaction of intermediate IV with thiol VII may be carried out over a wide temperature range, e.g. −15° C. up to room temperature, but is preferably done at a temperature in the range of from about −15° C. to +15° C., most preferably at around 0° C.

The carbapenem product produced by reaction of the quaternary amine thiol VII with intermediate IV will have a counter anion associated with it (i.e. $(C_6H_5O)_2$-$PO_2^{\ominus}$, $Cl^{\ominus}$ or the anion associated with the quaternary thiol) which may at this stage be substituted by a different counter anion, e.g. one which is more pharmaceutically acceptable, by conventional procedures. Alternatively, the counter anion may be removed during the subsequent de-blocking step. Where the quaternized carbapenem compound and counter anion form an insoluble product, the product may crystallize out as it is formed and be collected pure by filtration.

Following formation of the desired cabapenem product according to the above-described reaction step, the carboxyl protecting group $R^{2'}$ of compound I' may be optionally removed by conventional procedures as described above in connection with the general synthetic process.

The thiol intermediates of Formula VII may be prepared, for example, by reacting a sulfide of the formula

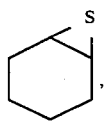 VIIIa

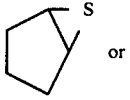 VIIIb or

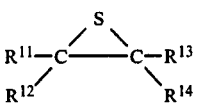 VIIIc wherein $R^{11}$, $R^{12}$, $R^{13}$ and $R^{14}$ are each independently hydrogen or $C_1$-$C_4$ alkyl with a heterocyclic amine (as defined above) of the formula

and a strong acid. The reaction may be carried out in the presence or absence of an inert organic solvent which is preferably a non-polar organic solvent such as methylene chloride, benzene, xylene, toluene or the like. Where the amine and sulfide reagents are liquids or where a solid amine is soluble in a liquid sulfide reagent, it is preferred to carry out the reaction without use of an additional solvent.

The particular strong acid used in the reaction is not critical and may be, for example, such strong inorganic or organic acids as hydrochloric, hydrobromic, methanesulfonic, p-toluenesulfonic, trifluoromethanesulfonic, etc.

Formation of the quaternary amine thiol intermediate VII may be carried out at a temperature in the range of from about −20° C. to about 100° C. Preferred temperatures are generally in the range of about 50°–70° C.

The sulfide reagent, aromatic amide and acid are preferably employed so that the sulfide and acid are used in approximately equimolar amounts with the amine being used in excess, e.g. two to three moles of amine per mole of sulfide or acid.

The quaternary amine thiol intermediate will have a counter anion associated with it which will be determined by the particular acid employed. It is, of course, possible to substitute at this point a different counter anion by conventional procedures for use in the subsequent reaction with carbapenem intermediate IV.

It will be understood that where the $R^1$ and/or $R^8$ substituent or the heterocyclic nucleophile attached to substituent A contain a functional group which might interfere with the intended course of reaction, such group may be protected by a conventional blocking group and then subsequently de-blocked to regenerate the desired functional group. Suitable blocking groups and procedures for introducing and removing such groups are well known to those skilled in the art.

In the case of certain compounds of formula I having a cycloalkylene or branched alkylene A substituent, one or more additional assymmetric carbon atoms may be created which result in formation of diastereoisomers. The present invention includes mixtures of such diastereoisomers as well as the individual purified diastereoisomers.

As in the case of other β-lactam antibiotics, compounds of general formula I may be converted by known procedures to pharmaceutically acceptable salts which, for purposes of the present invention, are substantially equivalent to the non-salted compounds. Thus, for example, one may dissolve a compound of formula I wherein $R^2$ is an anionic charge in a suitable inert solvent and then add an equivalent of a pharmaceutically acceptable acid. The desired acid addition salt may be recovered by conventional procedures, e.g. solvent precipitation, lyophilization, etc. Where other basic or acidic functional groups are present in the compound of formula I, pharmaceutically acceptable base addition salts and acid addition salts may be similarly prepared by known methods.

A compound of formula I where $R^2$ is hydrogen or an anionic charge, or a pharmaceutically acceptable salt thereof may also be converted by conventional procedures to a corresponding compound where $R^2$ is a physiologically hydrolyzable ester group, or a compound of formula I wherein $R^2$ is a conventional carboxyl protecting group may be converted to the corresponding compound where $R^2$ is hydrogen, an anionic charge or a physiologically hydrolyzable ester group, or a pharmaceutically acceptable salt thereof.

The novel carbapenem derivatives of general formula I wherein $R^2$ is hydrogen, an anionic charge or a physiologically hydrolyzable carboxyl protecting group, or the pharmaceutically acceptable salts thereof, are potent antibiotics active against various gram-positive and gram-negative bacteria and they may be used, for example, as animal feed additives for promotion of growth, as preservatives in food, as bactericides in industrial applications, for example in waterbased paint and in the white water of paper mills to inhibit the growth of harmful bacteria and as disinfectants for destroying or inhibiting the growth of harmful bacteria on medical and dental equipment. They are especially useful, however, in the treatment of infectious disease in humans and other animals caused by gram-positive or gram-negative bacteria.

The pharmaceutically active compounds of this invention may be used alone or formulated as pharmaceutical compositions comprising, in addition to the active carbapenem ingredient, a pharmaceutically acceptable carrier or diluent. The compounds may be administered by a variety of means; those of principal interest include: orally, topically or parenterally (intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain formulatory agents such as suspending, stabilizing and dispersing agents. The compositions may be in ready to use form or in powder form for reconstitution at the time of delivery with a suitable vehicle such as sterile water.

The dosage to be administered depends to a large extent on the particular compound being used, the particular composition formulated, the route of administration, the nature and condition of the host and the particular situs and organism being treated. Selection of the particular preferred dosage and route of application, then, is left to the discretion of the therapist. In general, however, the compounds may be administered parenterally or orally to mammalian hosts in an amount of from about 5 to 200 mg/kg/day. Administration is generally carried out in divided doses, e.g. three to four times a day.

To illustrate the potent broad-spectrum antibacterial activity of the carbapenems of the present invention, both in vitro and in vivo, and the low toxicity of the compounds, biological data is provided below relating to the presently preferred carbapenem compounds of the present invention.

IN VITRO ACTIVITY

A sample of the carbapenem compound of Example 1 after solution in water and dilution with Nutrient Broth was found to exhibit the following Minimum Inhibitory Concentrations (M.I.C.) in mcg/ml versus the indicated microorganisms as determined by overnight incubation at 37° C. by tube dilution. N-Formimidoyl thienamycin was included as a comparison compound.

In Vitro Antibacterial Activity of Carbapenem Derivative of Example 1

| Organism | | MIC (mcg/ml) | |
|---|---|---|---|
| | | New Compound | N—Formimidoyl Thienamycin |
| S. pneumoniae | A-9585 | 0.002 | 0.004 |
| S. pyogenes | A-9604 | 0.002 | 0.001 |
| S. aureus | A-9537 | 0.008 | 0.004 |
| S. aureus +50% serum | A-9537 | 0.016 | 0.016 |
| S. aureus (Pen-res.) | A-9606 | 0.016 | 0.008 |
| S. faecalis | A20688 | 1 | 0.5 |
| E. coli | A15119 | 0.03 | 0.016 |
| E. coli | A20341-1 | 0.03 | 0.03 |
| K. pneumoniae | A-9664 | 0.06 | 0.13 |
| K. pneumoniae | A20468 | 0.13 | 0.06 |
| P. mirabilis | A-9900 | 0.13 | 0.06 |
| P. vulgaris | A21559 | 0.03 | 0.03 |
| P. morganii | A15153 | 0.13 | 0.13 |
| P. rettgeri | A22424 | 0.25 | 0.25 |
| S. marcescens | A20019 | 0.06 | 0.03 |
| E. cloacae | A-9569 | 0.25 | 0.06 |
| E. cloacae | A-9656 | 0.13 | 0.06 |
| P. aeruginosa | A-9843A | 4 | 1 |
| P. aeruginosa | A21213 | 0.25 | 0.25 |
| B. fragilis | A22862 | 0.13 | 0.016 |
| B. fragilis | A22053 | 0.25 | 0.06 |
| B. fragilis | A22696 | 0.5 | 0.13 |
| B. fragilis | A22863 | 0.13 | 1 |

IN VIVO ACTIVITY

The in vivo therapeutic efficacy of the compound of Example 1 and N-formimidoyl thienamycin after intramuscular administration to mice experimentally infected with various organisms in shown in the following Table. The $PD_{50}$ (dose in mg/kg required to give protection to 50% of the infected mice) is indicated.

| | Protective Effect in the Intramuscular Treatment of Infected Mice | | |
|---|---|---|---|
| | | $PD_{50}$/Treatment (mg/kg) | |
| Organism | Challenge (No. of organisms) | Compound of Example 1 | N—Formimidoyl Thienamycin |
| P. mirabilis A-9900 | $4 \times 10^6$ | >10 | 3*/15* |
| P. aeruginosa A-9843a | $3 \times 10^6$ | 3 | 0.5* |

*Historical data
Treatment Schedule: Mice were treated i.m. with drugs 0 and 2 hours post-infection; 5 mice per dose were used for each test

TOXICITY

The toxicity of the compound of Example 1 after intracranial administration to mice was determined and is shown in the following Table.

| Compound | Toxicity After Intracranial Administration to Mice | |
|---|---|---|
| | *LD$_{50}$ (mg/kg) | Highest Dose (mg/kg) Without Clinical Signs of Toxicity |
| Compound of Example 1 | >10 | >10 |
| N—Formimidoyl Thienamycin | 32 | ~5 |

*Average of 25/mice/compound

BLOOD LEVELS IN MICE AFTER INTRAMUSCULAR ADMINISTRATION

Blood levels and the half-life of the compound of Example 1 after intramuscular administration of 20 mg/kg in mice are shown in the Table below.

| Compound | Blood Level (μg/ml) | | | | | | *t$_½$ (min) | **AUC (μg · h/ml) |
|---|---|---|---|---|---|---|---|---|
| | 10 | 20 | 30 | 45 | 60 | 90 | | |
| | Minutes after Administration | | | | | | | |
| Compound of Example 1 | 13.7 | 10.2 | 5.7 | 2.1 | <0.6 | <0.6 | 11 | 5.4 |
| N—Formimidoyl Thienamycin | 12.6 | 9.9 | 7.3 | 2.6 | 0.7 | <0.3 | 9 | 6 |

Compounds were solubilized in 0.1 M phosphate buffer pH 7. Values are from a single test; 4 mice used per compound.
*t$_½$ refers to half-life in minutes
**AUC refers to the area under the blood concentration-time curve The urinary recovery of the compound of Example 1 after intramuscular administration (20 mg/kg) to mice is shown in the following Table.

| Compound | Urinary Recovery After Intramuscular Administration of 20 mg/kg to Mice | | | |
|---|---|---|---|---|
| | Percentage of Dose Recovered | | | |
| | 0-3 | 3-6 | 6-24 | 0-24 |
| | Hours After Administration | | | |
| Compound of Example 1 | 18.8 | 0.6 | 0.1 | 19.5 ± 3.2 |
| N—Formimidoyl Thienamycin | 12.1 | 0.1 | <0.1 | 12.2 ± 3.6 |

Compounds were solubilized in 0.1 M phosphate buffer pH 7. Values are from a single test; 4 mice per compound.

Additional Biological Data

IN VITRO ACTIVITY

Samples of the carbapenem compounds indicated below (identified by example number) after solution in water and dilution with Nutrient Broth were found to exhibit the following Minimum Inhibitory Concentrations (M.I.C.) in mcg/ml versus the indicated microorganisms as determined by overnight incubation at 37° C. by tube dilution. N-formimidoyl thienamycin was included as a comparison compound.

| Organism | | Ex. 2 | MK 0787 | Ex. 3 | *MK 0787 | Ex. 4 | Ex. 5 (comp. B) | Ex. 5 (comp. A) | *MK 0787 |
|---|---|---|---|---|---|---|---|---|---|
| S. pneumoniae | A-9585 | 0.001 | 0.002 | 0.03 | 0.002 | 0.004 | 0.004 | 0.004 | 0.001 |
| S. pyogenes | A-9604 | 0.002 | 0.002 | 0.03 | 0.002 | 0.004 | 0.008 | 0.004 | 0.001 |
| S. faecalis | A20688 | 0.25 | 0.25 | 0.5 | 0.5 | 2 | 1 | 0.05 | 0.25 |
| S. aureus | A-9537 | 0.008 | 0.002 | 0.03 | 0.004 | 0.03 | 0.03 | 0.016 | 0.002 |
| S. aureus-50% serum | A-9537 | 0.016 | 0.016 | 0.13 | 0.016 | 0.06 | 0.06 | 0.03 | 0.004 |
| S. aureus (Pen-res.) | A-9606 | 0.016 | 0.008 | 0.03 | 0.008 | 0.06 | 0.06 | 0.03 | 0.004 |
| E. coli | A15119 | 0.016 | 0.016 | 0.03 | 0.016 | 0.13 | 0.13 | 0.03 | 0.016 |
| E. coli | A20341-1 | 0.03 | 0.016 | 0.03 | 0.03 | 0.13 | 0.13 | 0.03 | 0.016 |
| K. pneumoniae | A-9664 | 0.06 | 0.03 | 0.13 | 0.06 | 0.25 | 0.25 | 0.06 | 0.03 |
| K. pneumoniae | A20468 | 0.13 | 0.13 | 0.25 | 0.13 | 0.5 | 0.5 | 0.13 | 0.06 |
| E. cloacae | A-9659 | 0.13 | 0.13 | 0.25 | 0.06 | 1 | 0.5 | 0.13 | 0.06 |
| E. cloacae | A-9656 | 0.13 | 0.06 | 0.5 | 0.06 | 2 | 0.25 | 0.13 | 0.06 |
| P. mirabilis | A-9900 | 0.06 | 0.03 | 0.13 | 0.06 | 0.25 | 0.25 | 0.13 | 0.03 |
| P. vulgaris | A21559 | 0.03 | 0.016 | 0.03 | 0.03 | 0.25 | 0.25 | 0.06 | 0.016 |
| M. morganii | A15153 | 0.06 | 0.06 | 0.13 | 0.13 | 1 | 0.5 | 0.13 | 0.06 |
| P. rettgeri | A22424 | 0.13 | 0.13 | 0.5 | 0.13 | 1 | 1 | 0.25 | 0.13 |
| S. marcescens | A20019 | 0.06 | 0.03 | 0.06 | 0.03 | 0.25 | 0.25 | 0.06 | 0.03 |
| P. aeruginosa | A-9843a | 32 | 1 | 63 | 1 | 16 | 63 | 32 | 1 |
| P. aeruginosa | A21213 | 8 | 0.13 | 8 | 0.25 | 1 | 32 | 16 | 0.13 |

*N—formimidoyl thienamycin

IN VIVO ACTIVITY

The in vivo therapeutic efficacy of certain compounds of the present invention and N-formimidoyl thienamycin (MK 0787) after intramuscular administration to mice experimentally infected with various organisms is shown below. The PD$_{50}$ (dose in mg/kg required to give protection to 50% of the infected mice) is indicated.

| Protective Effect in the Intramuscular Treatment of Infected Mice | | | |
|---|---|---|---|
| | PD$_{50}$/treatment (mg/kg) | | |
| Compound (Example No.) | *P. aeruginosa* *A9843A | *P. aeruginosa* *A20481 | *S. aureus* *A-9606 |
| Ex. 2 | 4.7 | 33 | 0.72 |
| Ex. 5 comp. B | — | — | 0.39 |
| Ex. 5 comp. A | >12.5 | — | 1.2 |
| Ex. 4 | 2.7 | — | 1.6 |
| MK 0787 | 1 | 0.4 | 0.07 |

Treatment Schedule: °For compound of Ex. 2, mice were infected i.p. with $2 \times 10^9$ organisms (A9606), or $1 \times 10^5$ of A9843A and A20481. For compounds of Ex. 4 and 5, mice were infected i.p. with $\sim 9 \times 10^7$ organisms (A9606) or $\sim 8 \times 10^4$ (A98-43A). Mice were treated i.m. with drugs 0 and 2 h post-infection.

BLOOD LEVELS AND URINARY RECOVERY

Blood levels and the half-life of certain compounds of the present invention after intramuscular administration of 20 mg/kg in mice are shown below. Also shown is the urinary recovery in the mice.

| Pharmacokinetic Parameters in the Mouse After Intramuscular Dose of 20 mg/kg | | | | |
|---|---|---|---|---|
| | Blood | | | Urine |
| Compound (Example No.) | $C_{max}$ (μg/ml) | *$T_{\frac{1}{2}}$ (min) | AUC (μg · h/ml) | Recovery* % |
| Ex. 3 | 16.2 | 8 | 4.8 | 15 ± 3 |
| Ex. 4 | 17.3 | 12 | 7.6 | 33 ± 11 |
| Ex. 5 comp. A | 10.2 | 7 | 3.1 | 14 ± 1 |
| Ex. 5 comp. B | 12.6 | 10 | 4.6 | 15 ± 3 |
| MK 0787 | 14.6 | 10 | 6 | 33 ± 8 |

Compounds were solubilized in 0.1 M phosphate buffer, pH 7. Values based on a single test; 4 mice per compound.
*$T_{\frac{1}{2}}$ refers to half-life in minutes
**AUC refers to the area under the blood concentration-time curve
***Recovery based on 0-6 hour collection

EXAMPLE 1

Preparation of 3-[2-(N-methylpyrrolidinium)ethylthio]-6α-[1-(R)-hydroxyethyl]-7-oxo-1-azabicyclo[3.2.0]hept-2-ene-2-carboxylate

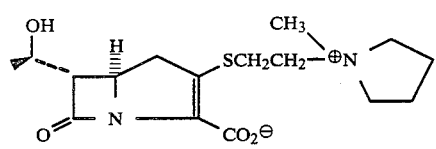

A. p-Nitrobenzyl 3-(2-hydroxyethylthio)-6α-[1-(R)-hydroxyethyl]-7-oxo-1-azabicyclo[3.2.0]hept-2-ene-2-carboxylate

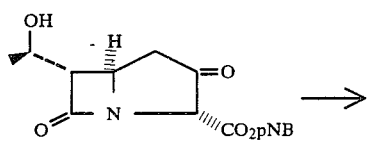

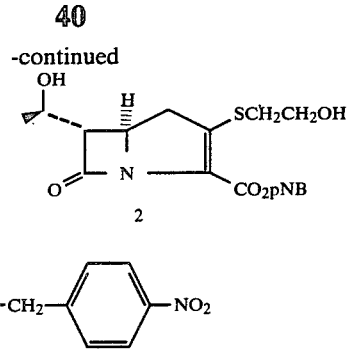

A solution of 1.69 g (4.85 mmol) of p-nitrobenzyl 6α-[1-(R)-hydroxyethyl]-3,7-dioxo-1-azabicyclo(3.2.0-)hept-2-ene-2-carboxylate (1) in 20 ml of acetonitrile was cooled to 0° C. under a nitrogen atmosphere. A solution of 726 mg (7.18 mmol) of diisopropylethylamine in 2 ml of acetonitrile was added followed by a dropwise addition of 1.51 g (5.60 mmol) of diphenyl chlorophosphate in 12 ml of acetonitrile over a period of 3 minutes. The resulting solution was stirred at 0° for 20 minutes to provide p-nitrobenzyl 3-(diphenylphosphoryloxy)-6α-(1-(R)-hydroxyethyl]-7-oxo-1-azabicyclo(3.2.0)hept-2-ene-2-carboxylate. To this solution was added a solution of 726 mg (7.18 mmol) of diisopropylethylamine in 2 ml of acetonitrile followed by a solution of 439 mg (5.63 mmol) of 2-mercaptoethanol in 2 ml of acetonitrile. The reaction solution was stirred at 0° C. for 3 hours and then diluted with 200 ml of ethyl acetate and washed with 200 ml of water, 100 ml of 20% aqueous H$_3$PO$_4$, and brine. Evaporation of the dried (MgSO$_4$) solution gave a semisolid which was triturated with methylene chloride and filtered to yield 1.2 g (61% yield) of title product 2 as a white amorphous solid.

NMR (DMSO-d6) δ: 1.20 (3H, d, J=6.0 Hz), 2.9–3.2 (9H, m), 5.22 (1H, d, J=8.5 Hz) and 8.23 (2H, d, J=8.5 Hz); ir (KBr) Γmax: 3500, 1770 and 1700 cm$^{-1}$; Anal. Calc'd for C$_{18}$H$_{20}$N$_2$O$_7$S: C, 52.93; H, 4.94; N, 6.86; S, 7.85. Found: C, 52.83; H, 4.90; N, 6.42; S, 8.31.

B. p-Nitrobenzyl 3-(2-methanesulfonyloxyethylthio)-6α-[1-(R)-hydroxyethyl]-7-oxo-1-azabicyclo(3.2.0-)hept-2-ene-2-carboxylate

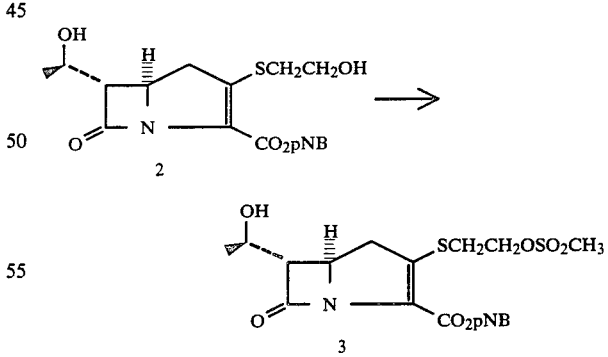

To a solution of 4.2 g (10.3 mmol) of 2 in 200 ml of tetrahydrofuran there was added at −40° C. 1.3 g (11.3 mmol) of methanesulfonyl chloride followed by a dropwise addition of 1.26 g (12.4 mmol) of triethylamine in 5 ml of tetrahydrofuran. The reaction mixture was stirred for 5 hours at −40° C., then stirred for 2 hours at −30° C. under a nitrogen atmosphere and then poured into a mixture of ethyl acetate (700 ml) and 5% aqueous phosphoric acid (1000 ml). The organic layer was washed with brine, dried over MgSO4, filtered and condensed to a syrup. This material was purified by silica gel column chromatography [elution with methylene chloride-ethyl acetate (3:1 v/v)] to give 3.55 g (75% yield) of the title compound as a white amorphous solid.

NMR (CDCl3) δ: 1.25 (3H, d, J=6.0 Hz), 3.05 (3H, s), 3.06–3.40 (5H, m), 4.05–4.40 (4H, m), 5.25 (1H, d, J=14.0 Hz), 5.50 (1H, d, J=14.0 Hz), 7.70 (2H, d, J=8.5 Hz) and 8.23 (2H, d, J=8.5 Hz); ir (KBr) γmax: 3400, 1770 and 1600 cm$^{-1}$. Anal. Calc'd for C19H22N2O9S2: C, 46.90; H, 4.56; N, 5.76. Found: C, 46.52; H, 4.32; N, 5.91.

C. p-Nitrobenzyl 3-(2-iodoethylthio)-6α-[1-(R)-hydroxyethyl]-7-oxo-1-azabicyclo(3.2.0)hept-2-ene-2-carboxylate

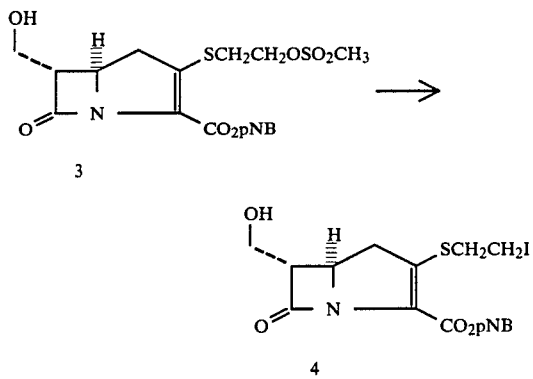

A solution of 350 mg (0.72 mmol) of intermediate 3 and 216 mg (1.4 mmol) of sodium iodide in 20 ml of acetone was heated at reflux for 4 hours. Evaporation of the acetone gave a white amorphous solid which was suspended in ether (10 ml)-water (10 ml). Filtration of the white solid and vacuum drying produced 300 mg (80% yield) of the title compound 4 as a white amorphous powder.

NMR (DMSO-d6) δ: 1.18 (3H, d, J=6.0 Hz), 3.20–3.60 (7H, m), 3.80–4.25 (2H, m), 5.10 (1H, d, J=5.5 Hz), 5.25 (1H, d, J=12.0 Hz), 5.45 (1H, d, J=12.0 Hz), 7.70 (2H, d, J=8.5 Hz), and 8.27 (2H, d, J=8.5 Hz); ir (KBr) γmax: 3500, 1768 and 1700 cm$^{-1}$; Anal. Calc'd for C18H19N2O6I: C, 41.71; H, 3.70; N, 5.41; I, 24.48. Found: C, 42.10; H, 3.75; N, 5.97; I, 23.20.

D. 3-[2-(N-methylpyrrolidinium)ethylthio]-6α-[1-(R)-hydroxyethyl]-7-oxo-1-azabicyclo[3.2.0]hept-2-ene-2-carboxylate

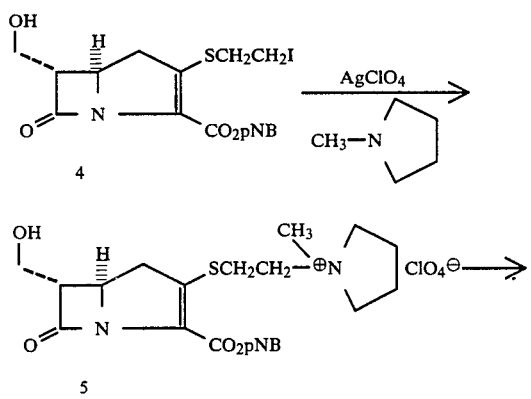

To a cooled (5° C.) solution of p-nitrobenzyl 3-(2-iodoethylthio)-6α-[1-(R)-hydroxyethyl]-7-oxo-1-azabicyclo[3.2.0]hept-2-ene-2-carboxylate (728 mg; 1.4 mmol) in 60 ml of dry tetrahydrofuran, there was added N-methylpyrrolidine (301 mg; 3.5 mmol) followed by a solution of silver perchlorate (560 mg; 2.8 mmol) in 5 ml of tetrahydrofuran. The reaction mixture was stirred for 60 minutes at 5° C. The solvent was then evaporated in vacuo affording compound 5 as a yellow gum. This gum was digested with 2 g of CELITE to give an amorphous solid. IR(KBr) γmax: 3400, 1775, 1700 and 1100 cm$^{-1}$. Without any further purification, compound 5 was hydrogenated as follows:

To a suspended solution of compound 5 in 50 ml of diethyl ether and 100 ml of tetrahydrofuran, there was added a solution of potassium bicarbonate (320 mg; 3.2 mmol) and dibasic potassium phosphate (280 mg; 1.6 mmol) in 125 ml of water. Then, 1 g of 10% palladium on charcoal was added and the mixture was hydrogenated at 40 psi on the Parr shaker for 60 minutes. The mixture was then filtered and the catalyst was washed with water (2×10 ml). The combined filtrate and washing was extracted with diethyl ether (2×200 ml) and then lyophilized to give a brown powder. This crude material was purified on a C18 BONDAPAK reverse phase column (8 g) (Waters Associates), eluting with water under a 8 psi pressure. Each fraction (20 ml) was screened by high pressure liquid chromatography, and fractions having an ultraviolet absorption λmax 300 nm were collected and lyophilized to give 65 mg (14% yield based on compound 4) of title compound as a white solid.

NMR (D2O) δ: 1.23 (3H, d, J=6.0 Hz), 2.1–2.4 (4H, m), 3.10 (3H, s), 3.1~3.4 (12H, m), 3.95−4.30 (2H, m); IR (KBr) γmax: 3400, 1760 and 1590 cm$^{-1}$. UVλ$_{max}$ (CH3CH2OH) 297 nm (E=6877).

EXAMPLE 2

Preparation of 3-[2-(N-Methyl-thiomorpholinium)ethylthio]-6α-[1'-(R)-hydroxyethyl]-7-oxo-1-azabicyclo[3.2.0]-hept-2-ene-2-carboxylate

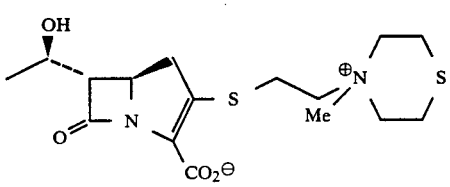

A. N-methyl-N-(2-mercaptoethyl)-thiomorpholinium methanesulfonate

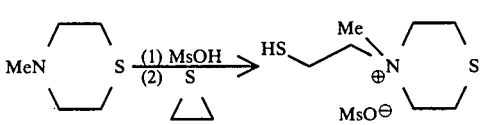

To precooled (ice bath) N-methylthiomorpholine* (5.00 g, 42.7 mmol) was added methanesulfonic acid (1.47 mL, 20.5 mmol) and ethylene sulfide (1.30 mL, 21.4 mmol). The mixture was heated at 65° C. for 24 h and diluted with water (25 mL). The aqueous solution was washed with diethyl ether (3×25 mL), pumped under vacuum and poured over a silica gel reverse phase column; the title compound being eluted with water. The appropriate fractions were combined and evaporated to afford the thiol as an oil (4.80 g, yield 86%); ir (film) $v_{max}$: 2550 cm$^{-1}$ (w, SH); $^1$Hmr (DMSO d$_6$)δ: 3.25–2.95 (6H, m, CH$_2$N⊕), 3,32 (3H, s, CH$_3$N⊕), 3.20–2.65 (7H, m, CH$_2$S, SH) and 2.32 ppm (3H, s, CH$_3$SO$_3$).

*J. M. Lehn and J. Wagner. Tetrahedron, 26, 4227 (1970)

B. para-Nitrobenzyl 3-[2-(N-methyl-thiomorphonilium diphenyl phosphate)ethylthio]-6α-[1'-(R)-hydroxyethyl]-7-oxo-1-azabicyclo[3.2.0]-hept-2-ene-2-carboxylate

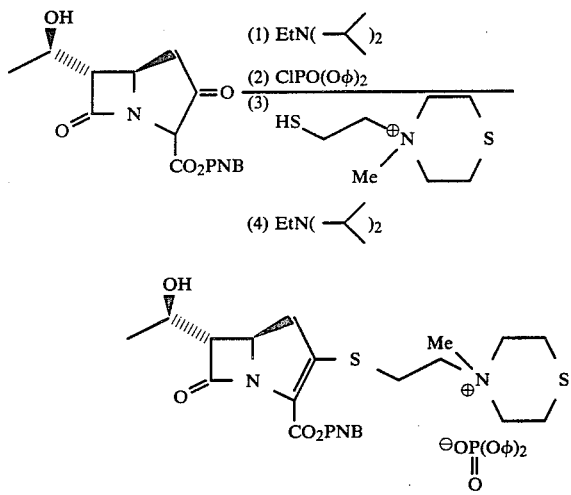

A cold (ice bath) solution of para-nitrobenzyl 6α-[1'-(R)-hydroxyethyl]-3,7-dioxo-1-azabicyclo[3.2.0]heptane-2-carboxylate (557 mg, 1.60 mmol) in CH$_3$CN (8 mL) was treated dropwise with diisopropylethyl amine (0.336 mL, 1.92 mmol) and diphenylchlorophosphate (0.400 mL, 1.92 mmol) and stirred for 30 min. The reaction mixture was treated again with N-methyl-N-(2-mercaptoethyl)thiomorpholinium methanesulfonate (893 mg, 2.29 mmol) in CH$_3$CN (4 mL) and diisopropylethyl amine (0.336 mL, 1.92 mmol) and stirred for 30 min. The solution was diluted with water (20 mL) and poured over a silica gel reversed phase column. The desired compound was eluted with a 50% acetonitrile-water mixture. The appropriate fractions were combined, pumped under vacuum for 2 h. and lyophylized to afford the title compound (1.01 g, yield 85%): ir (nujol)$v_{max}$: 1760 (s, β-lactam C=O) and 1510 cm$^{-1}$ (s, NO$_2$); $^1$Hmr (DMSO-d$_6$) δ: 8.25 (2H, d, J=8.8 Hz, H-aromatic), 7.70 (2H, d, J=8.8 Hz, H-aromatic), 7.33–6.84 (10H, m, H-aromatic), 5.37 (2H, center of ABq, J=14.2 Hz, CH$_2$), 5.14 (1H, d, J=4.5 Hz, OH), 4.35–3.80 (2H, m, H-1' and H-5), 3.75–3.45 (6H, m, CH$_2$N+), 3.31 (3H, s, CH$_3$N+), 3.45–2.75 (9H, m, CH$_2$S, H-6 and H-4) and 1.15 ppm (3H, d, J=6.2 Hz, CH$_3$).

C. 3-[2-(N-methyl-thiomorpholinium)ethylthio]-6α-[1'-(R)-hydroxyethyl]-7-oxo-1-azabicyclo[3.2.0]-hept-2-ene-2-carboxylate

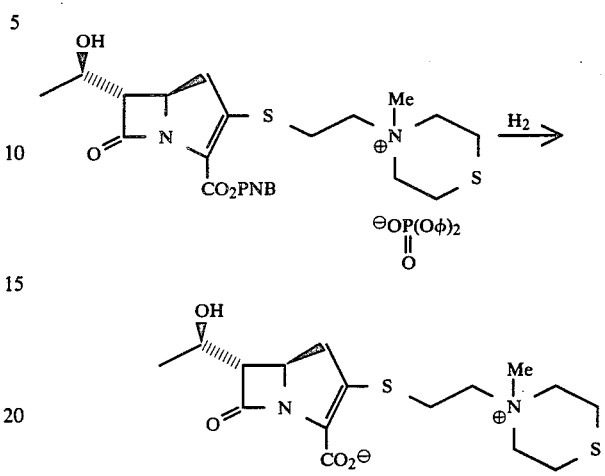

A solution of para-nitrobenzyl 3-[2-(N-methylthiomorpholinium diphenylphosphate)ethylthio]-6α-[1'-(R)-hydroxyethyl]-7-oxo-1-azabicyclo[3.2.0]hept-2-ene-2-carboxylate (1.31 g, 1.76 mmol) in 0.1M pH 7.4 phosphate buffer (48.8 mL), tetrahydrofuran (20 mL) and diethyl ether (20 mL) was hydrogenated over 10% pd/C (1.5 g) in a Parr shaker for 1 h at 40 psi. The reaction mixture was diluted with diethyl ether (40 mL) and the phases were separated. The organic phase was washed with water (2×5 mL). The aqueous phases were combined, filtered through a #52 hardened filter paper, washed with diethyl ether (2×20 mL) and pumped under vacuum. The aqueous solution was poured on a silica gel reverse phase column and the desired carbapenem was eluted with 5% acetonitrile-water. The appropriate fractions were combined, and lyophilized to give title compound as an amorphous solid (205 mg, 31%); ir (nujol)$v_{max}$: 1750 (s, β-lactam C=O) and 1590 cm$^{-1}$ (s, C=O); $^1$Hmr (D$_2$O) δ: 4.25–3.95 (2H, m, H-1', H-5), 3.70–3.40 (6H, m, CH$_2$N+), 3.35 (1H, dd, J=6.1 Hz, J=2.6 Hz, H-6), 3.08 (3H, s, CH$_3$N+), 3.25–2.75 (8H, CH$_2$S, H-4), and 1.24 ppm (3H, d, J=6.4 Hz, CH$_3$); uv (H$_2$O, c 0.062)$\lambda_{max}$: 299 (ε10,962) T½ 17.7 h (0.1M pH 7 phosphate buffer, 37° C.).

EXAMPLE 3

Preparation of (5R,6S)-3-[2-(1-methylmorpholino)ethylthio]-6-[(R)-1-hydroxyethyl]-7-oxo-1-azabicyclo[3.2.0]hept-2-ene-2-carboxylate

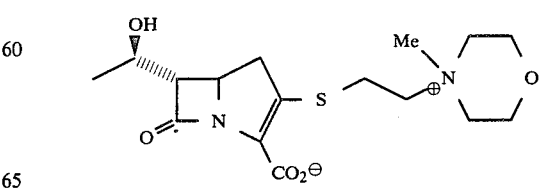

A. 1-Methyl-1-(2-mercaptoethyl)morpholinium trifluoromethanesulfonate

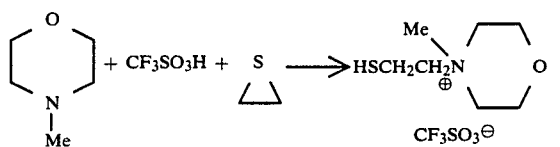

To N-methylmorpholine (3.29 mL, 0.030 mol) was added dropwise trifluoromethanesulfonic acid (1.327 mL, 0.015 mol) at 10° C., followed by ethylene sulfide (0.89 mL, 0.015 mol). The resulting yellow-brown solution was heated (oil bath) at 50°–60° C. under $N_2$ for 18 h. Volatile material was then removed in vacuo and the residual oil was taken up in 10 mL of $H_2O$. The aqueous solution was washed with diethyl ether (3×5 mL) and then residual organic solvent was removed in vacuo. The resulting aqueous solution was applied to a $C_{18}$ reverse-phase column which was eluted with $H_2O$, then 5% acetonitrile-$H_2O$ and finally 10% acetonitrile-$H_2O$. Evaporation of the relevant fractions afforded a white solid which was dried in vacuo ($P_2O_5$) to give the product (1.92 g, 41%). ir (KBr)$\nu_{max}$: 2560 (—SH) cm$^{-1}$; $^1$Hnmr (d$_6$-acetone) δ: 4.25–3.6 (m, 8H), 3.49 (s, 3H, N-Me), 3.35–2.7 (m, 5H).

B. p-Nitrobenzyl (5R,6S)-3-[2-(1-methylmorpholino)ethylthio]-6-[(R)-1-hydroxyethyl]-7-oxo-1-azabicyclo[3.2.0]hept-2-ene-2-carboxylate diphenylphosphate

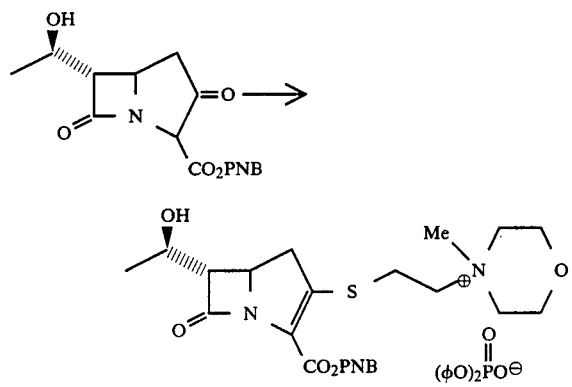

To a solution of p-nitrobenzyl (5R,6S)-6-[(R)-1-hydroxyethyl]-3,7-dioxo-1-azabicyclo[3.2.0]heptane-2-carboxylate (0.348 g, 1.0 mmol) in 25 mL of dry acetonitrile was added dropwise diisopropylethylamine (0.191 mL, 1.1 mmol) and then diphenyl chlorophosphate (0.228 mL, 1.1 mmol) at 0° C. under $N_2$. After stirring at 0° C. for 1 h diisopropylethylamine (0.226 mL, 1.3 mmol) was added to the resulting enol phosphate, followed by 1-methyl-1-(2-mercaptoethyl)morpholinium trifluoromethanesulfonate (0.373 1 g, 1.2 mmol). The reaction mixture was stirred at room temperature for 1.5 h and then concentrated in vacuo. The residual material was taken up in $H_2O$ and applied to a $C_{18}$ reverse-phase column. Elution with $H_2O$, then 20% acetonitrile-$H_2O$ and finally 30% acetonitrile-$H_2O$ followed by lyophilization of the relevant fractions gave the product (0.360 g, 40%) as an amorphous solid. ir (film) 3300 (—OH), 1770 (β-lactam CO), 1700 (—CO$_2$PNB) cm$^{-1}$; $^1$Hnmr (d$_6$-acetone) δ: 8.25, 7.80 (ABq, J=8.6 Hz, 4H, aromatic), 7.4–6.8 (m, 10H, diphenylphosphate), 5.56, 5.27 (ABq, J=14.2 Hz, 2H, benzylic), 4.42 (d of t, J=9.2 Hz, J'=2.7 Hz, 1H, H-5), 4.1–2.7 (m, 17H), 3.40 (s, 3H, N-Me), 1.22 (d, J=6.2 Hz, 3H, —CHMe).

C. (5R,6S)-3-[2-(1-methylmorpholino)ethylthio]-6-[(R)-1-hydroxyethyl]-7-oxo-1-azabicyclo[3.2.0]hept-2-ene-2-carboxylate

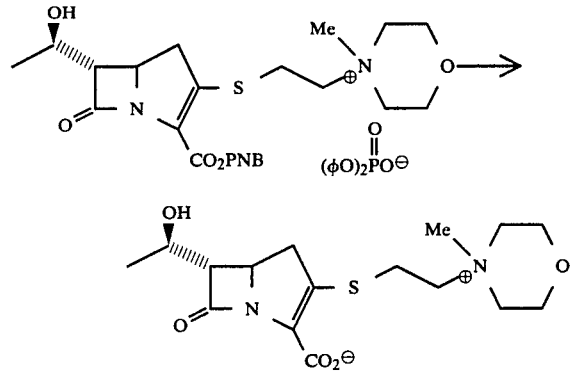

To a solution of p-nitrobenzyl (5R,6S)-3-[2-(1-methylmorpholino)ethylthio]-6-[(R)-1-hydroxyethyl]-7-oxo-1-azabicyclo[3.2.0]hept-2-ene-2-carboxylate diphenylphosphate (0.360 g, 0.49 mmol) in 13 mL of phosphate buffer (0.05M pH 7.4) was added 0.36 g of 10% palladium-on-charcoal, 20 mL of tetrahydrofuran and 20 mL of diethyl ether. This mixture was hydrogenated (Parr) at 32 psi for 1 h. The mixture was filtered through Celite and the filter pad was washed with $H_2O$ and diethyl ether. The aqueous phase was separated and the pH was adjusted to 7.0 with additional pH 7.4 phosphate buffer. After removing residual organic solvents in vacuo the aqueous solution was applied to $C_{18}$ reverse-phase column. Elution with $H_2O$ and lyophilization of the relevant fractions afforded 0.130 g of an amorphous solid. This material was repurified by reverse-phase hplc to give the pure product (0.058 g, 34%) as an amorphous solid. ir (KBr)$\nu_{max}$: 3420 (br, OH), 1750 (β-lactam CO), 1590 (—CO$_2^-$) cm$^{-1}$; $^1$Hnmr (D$_2$O) δ: 4.35–2.77 (m, 17H), 3.18 (s, 3H, N-Me), 1.23 (d, J=6.3 Hz, 3H, CHMe); uv (H$_2$O)$\lambda_{max}$: 300 (ε6344) nm; t$_{\frac{1}{2}}$ (pH 7.4, 36.8° C.) 18.5 h.

EXAMPLE 4

Preparation of (5R,6S)3-[2-(1,4-dimethyl-1-piperazinium)ethylthio]-6-[1-(R)-hydroxyethyl]-7-oxo-1-azabicyclo[3.2.0]hept-2-ene-2-carboxylate

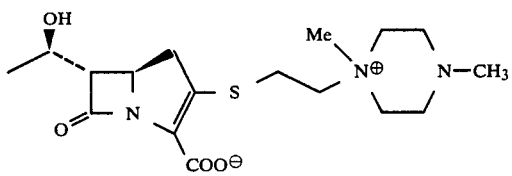

A. 1-(2-acetylthioethyl)-1,4-dimethylpiperazinium bromide

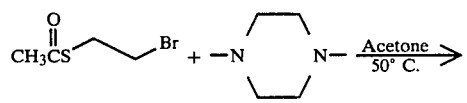

-continued

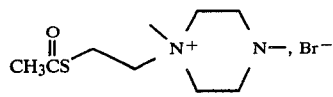

A solution of 2-bromoethyl thiolacetate *(2.20 g, 0.012 mol) and 1,4-dimethylpiperazine (1.95 mL, 0.014 mol) in acetone (4 mL) was stirred at 50° C. for 65 h. After cooling to 25° C., the liquid phase was decanted from the gum which was triturated twice in diethyl ether; a hygroscopic yellowish powder, 3.2 g (90%) was obtained; ir (Nujol) $\nu_{max}$: 1685 (C=O of thioester) cm$^{-1}$; $^1$Hmr (D$_2$O) δ:

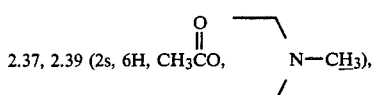

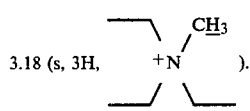

*B. Hansen, Acta Chem. Scand. 11, 537–40 (1957)

B. 1,4-dimethyl-1-(2-mercaptoethyl)piperazinium bromide hydrochloride

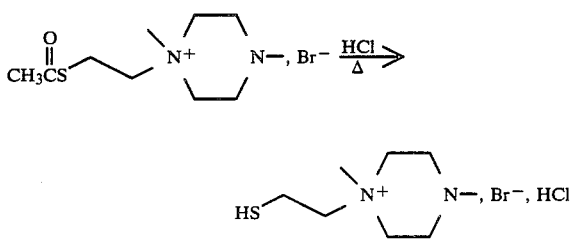

A solution of 1-(2-acetylthioethyl)-1,4-dimethylpiperazinium bromide (1.1 g, 3.7 mmol) in 6N hydrochloric acid (4 mL) was heated at 80° C. under a nitrogen atmosphere for 1 h. The solution was concentrated under reduced pressure to give a white powder, 0.41 g (38%), $^1$Hmr (DMSO, d$_6$) δ:

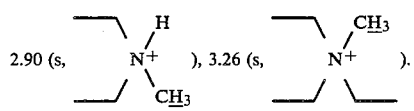

Anal. calcd. for C$_8$H$_{20}$N$_2$SBrCl.H$_2$O: C 31.03, H 7.16, N 9.05, S 10.35; found: C 31.62, H 7.46, N 9.19, S 10.19.

C. (5R,6S)Paranitrobenzyl 3-[2-(1,4-dimethyl-1-piperazinium)ethylthio]-6-[1-(R)-hydroxyethyl]-7-oxo-1-azabicyclo[3.2.0]-hept-2-ene-2-carboxylate diphenylphosphate

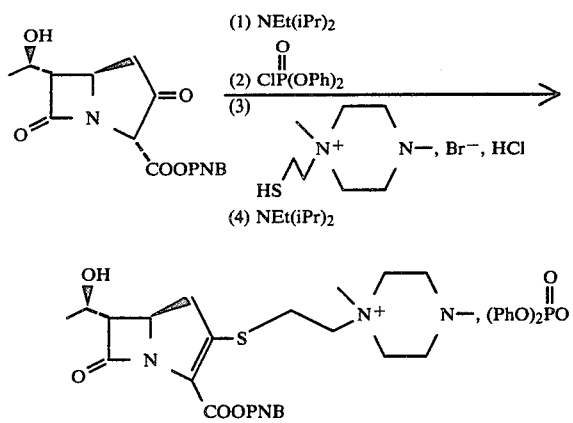

To a cold (0° C.) solution (5R,6S)paranitrobenzyl 6-[1-(R)-hydroxyethyl]-3,7-dioxo-1-azabicyclo[3.2.0-]heptane-2-(R)-carboxylate (0.465 g, 1.33 mmol) in acetonitrile (2 mL) kept under a nitrogen atmosphere was added diisopropylethylamine (0.278 mL, 1.59 mmol) and diphenyl chlorophosphate (0.33 mL, 1.59 mmol). The reaction mixture was stirred for 30 min and treated with a suspension of 1,4-dimethyl-1-(2-mercaptoethyl)-piperazinium bromide hydrochloride (0.40 g, 1.37 mmol) in acetonitrile (3 mL)-water (1 mL) mixture and diisopropylethylamine (0.278 mL, 1.59 mmol). After stirring for 18 h at 5° C., cold water (15 mL) was added to the mixture. The resulting solution was chromatographed over PrePak-500/C$_{18}$ (Waters Associates) column (2.5×7.5 cm) with 25–35% acetonitrile in water as eluting solvents to give a yellowish powder 0.50 g (50%) after lyophylization; ir (KBr) $\nu_{max}$: 1765 (C=O of β-lactam), 1690 (C=O of PNB ester), 1585 (phenyl), 1512 (NO$_2$), 875 (NO$_2$) cm$^{-1}$, $^1$Hmr (DMSO, d$_6$) δ: 1.16, 1.18 (2d, J=6.1 Hz, 3H, CH$_3$CHOH), 2.44

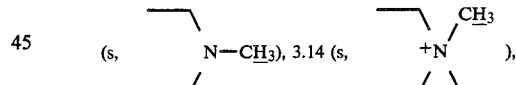

5.31 (d, J=6 Hz, OH), 5.39 (center of ABq, J=13 Hz, CH$_2$ of PNB), 6.6–7.4 (m, 10H, phenyl of phosphate), 7.71 (d, J=8.8 Hz, 2H, Ho of PNB), 8.26 (d, J=8.8 Hz, Hm of PNB).

D. (5R,6S)3-[2-(1,4-dimethyl-1-piperazinium)ethylthio]-6-[1-(R)-hydroxyethyl]-7-oxo-1-azabicyclo[3.2.0-]hept-2-ene-2-carboxylate

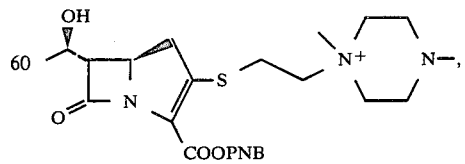

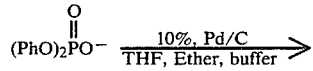

-continued

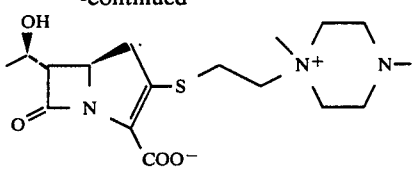

To a solution of (5R,6S)paranitrobenzyl 3-[2-(1,4-dimethyl-1-piperazinium)ethylthio]-6-[1-(R)-hydroxyethyl]-7-oxo-1-azabicyclo[3.2.0]hept-2-ene-2-carboxylate diphenylphosphate (0.47 g, 0.623 mmol) in wet tetrahydrofuran (25 mL) was added diethyl ether (25 mL), potassium phosphate monobasic-sodium hydroxide buffer (13 mL, pH 7.22) and 10% palladium on charcoal (0.47 g). The resulting mixture was hydrogenated at 23° C. under 40 psi for 1 h. The two layers were separated and the organic layer was extracted with water ($2 \times 7$ mL). The aqueous layers were combined, filtered through a Celite pad, washed with diethylether ($2 \times 15$ mL) and chromatographed on PrePak-500/$C_{18}$ (Waters Associates) column ($2.5 \times 9.5$ cm) with water as eluting solvent to give, 0.097 g (43%) after lyophylization; ir (KBr) $\nu_{max}$: 3000–3700 (OH), 1750 (C=O of $\beta$-lactam), 1585 (carboxylate) cm$^{-1}$, $^1$Hmr (D$_2$O) $\delta$: 1.24 (d, J=6.4 Hz, 3H, CH$_3$CHOH), 2.33

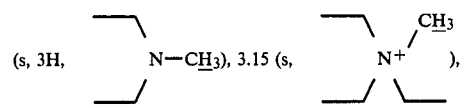

(s, 3H, N—C$\underline{H}_3$), 3.15 (s, N$^+$ $\diagdown$CH$_3$ ), 4.0–4.5 (m, H-5, CH$_3$CHOH), uv (H$_2$O) $\lambda_{max}$: 296 ($\epsilon$9476), [$\alpha$]$_D^{23}$ 61.1° (C 0.6, H$_2$O), t$\frac{1}{2}$=12.4 h (measured at a concentration of $10^{-4}$M in phosphate buffer pH 7.4 at 36.8° C.).

EXAMPLE 5

Preparation of (5R,6S)-3-[2-(N-methyl-thiomorpholiniumoxide)ethylthio]-6-[1-(R)-hydroxyethyl]-7-oxo-1-azabicyclo(3.2.0)-hept-2-ene-2-carboxylate

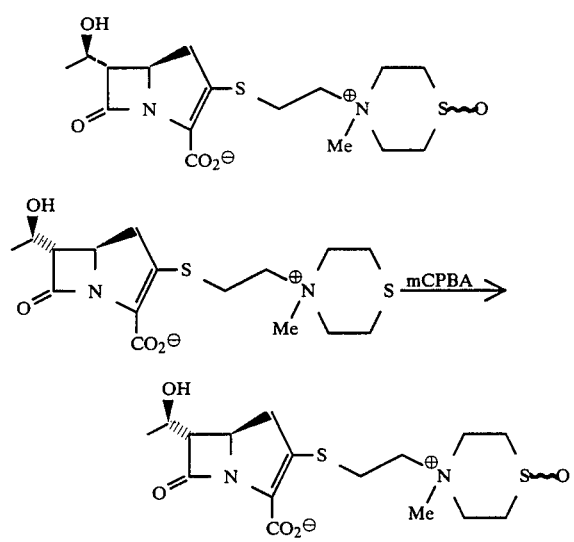

To a cold ($-10°$ C.) solution of (5R,6S)-3-[2-(N-methyl-thiomorpholinium)ethylthio]-6-[1-(R)-hydroxyethyl]-7-oxo-1-azabicyclo(3.2.0)-hept-2-ene-2-carboxylate (608 mg, 1.65 mmol) in a 1:1 mixture of acetonitrile-water (9 mL) was added m-chloroperbenzoic acid (334.8 mg, 1.65 mmol) in small portion over a 1 hour period. The mixture was then diluted with water (15 mL) and washed with diethyl ether ($3 \times 15$ mL). The aqueous phase was pumped under vacuum and passed through a reversed phase silica gel column (H$_2$O) to give a solid which consisted of a mixture of compounds. This mixture was separated by reversed phase HPLC and afforded fraction A 52.4 mg (yield 12%) and fraction B 23.6 mg (yield 6%) as diastereomers of the title compound; Fraction A: ir (nujol) $\nu_{max}$: 1750 (s, $\beta$-lactam C=O) and 1580 cm$^{-1}$ (s, C=O); $^1$Hmr (D$_2$O) $\delta$: 4.26–2.91 (20H, m, H-4, H-5, H-6, H-1', CH$_2$S, CH$_2$S—O, CH$_3$—N$^+$ and CH$_2$N$^+$) and 1.24 ppm (3H, d, J=6.4 Hz, CH$_3$); uv (H$_2$O, c 0.06) $\lambda_{max}$: 302 ($\epsilon$10425); T $\frac{1}{2}$:12 h (0.065M, pH 7.4 phosphate buffer, 37° C.). Fraction B: ir (nujol) $\nu_{max}$: 1750 (s, $\beta$-lactam C=O) and 1585 cm$^{-1}$ (s, C=O); $^1$Hmr (D$_2$O) $\delta$: 3.86–2.90 (17 H, m, H-4, H-5, H-6, H-1', CH$_2$S, CH$_2$S—O, CH$_2$N$^+$), 3.25 (3H, s, CH$_3$N$^+$) and 1.24 ppm (3H, d, J=6.4 Hz, CH$_3$); uv (H$_2$O, c 0.05) $\lambda_{max}$: 2.99 ($\epsilon$6517); T $\frac{1}{2}$:10.75 h (0.065M, pH 7.4 buffer solution, 37° C.).

EXAMPLE 6

Preparation of (5R,6S)-3-[2-(1,4,4-Trimethyl-1-piperazinium)ethylthio]-6-[1R-hydroxyethyl]-7-oxo-1-azabicyclo(3.2.0)hept-2-ene-2-carboxylate chloride

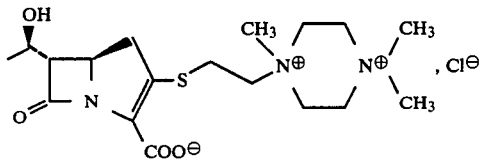

A. 1-(2-acetylthioethyl)-1,4,4-trimethylpiperazinium bromideiodide

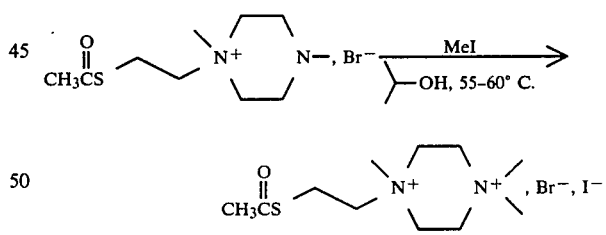

A suspension of 1-(2-acetylthioethyl)-1,4-dimethylpiperazinium bromide (1.48 g, 5.0 mmol) in isopropyl alcohol (10 mL) was treated with methyliodide (0.373 mL, 6.0 mmol) and heated at 55°–60° C. for 30 h. The solvents were evaporated under reduced pressure; the residue was triturated in hexane and the solid was filtered, 1.85 g. The solid was dissolved in hot water (8 mL) and the solution was diluted with acetone until turbidity (70–80 mL). Two successive crystallizations gave 1.5 g, mp 220°–5° C. dec., 68% of the title compound; ir (KBr)$\nu_{max}$: 1692 cm$^{-1}$ (C=O); $^1$Hmr (D$_2$O) $\delta$: 2.40 (s, 3H, CH$_3$COO), 3.37 (s, N—CH$_3$), 3.39 (s, N—CH$_3$), 3.99 (s); uv (H$_2$O)$\lambda_{max}$: 226 ($\epsilon$13144). Anal. calcd for C$_{11}$H$_{24}$N$_2$OSBrI: C 30.08, H, 5.51, N 6.38; found: C 30.48, H 5.53, N 6.86.

B. 1-(2-mercaptoethyl)-1,4,4-trimethylpiperazinium bischloride

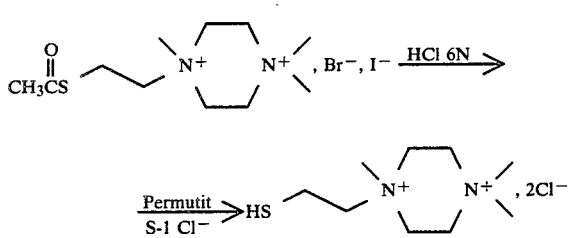

A mixture of 1-(2-acethylthioethyl)-1,4,4-trimethylpiperazinium bromideiodide (1.84 g, 4.19 mmol) and 6N hydrochloric acid (15 mL) was heated at 57° C. under a nitrogen atmosphere for 2.5 h. The solution was concentrated under reduced pressure to dryness. The solid was suspended in water (10 mL) and the well-stirred suspension was treated with permutit S-1 Cl⁻ until a solution was obtained. The solution was poured on a column (1.2×60 cm) of permutit S-1 Cl⁻. The column was eluted with water (1.5 mL/min). The appropriate fractions were combined and lyophilized to give a white powder, 0.93 g, mp 190°–191° C., 85%; ir (nujol)$v_{max}$: 2460 (SH); ¹Hmr (D₂O) δ: 3.4 (s, N—CH₃), 3.45 (s, N—CH₃), 4.07 (s). Anal. calcd for C₉H₂₂N₂SCl₃.0.75 H₂O: C 39.34, H 8.62, N 10.20, S 11.67; found: C 39.48, H 8.39, N 10.55, S 11.15.

C. (5R,6S)paranitrobenzyl 3-[2-(1,4,4-trimethyl-1-piperazinium)ethylthio]-6-(1R-hydroxyethyl)-7-oxo-1-azabicyclo(3.2.0)hept-2-ene-2-carboxylate bischloride

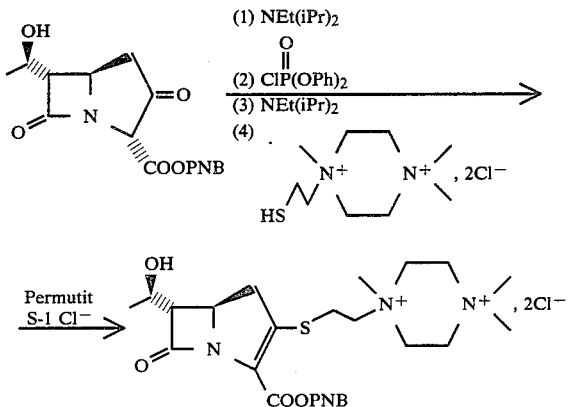

To a cold (5° C.) solution of (5R,6S)paranitrobenzyl 6-[1R-hydroxyethyl]-3,7-dioxo-1-azabicyclo(3.2.0)heptane-2R-carboxylate (0.94 g, 2.7 mmol) in acetonitrile (3 mL) kept under a nitrogen atmosphere was added diisopropylethylamine (0.557 mL, 3.2 mmol) and diphenyl chlorophosphate (0.663 mL, 3.2 mmol). The reaction mixture was stirred at 5° C. for 30 min and treated with diisopropylethylamine (0.599 mL, 3.44 mmol) and an aqueous solution (4 mL) of 1-(2-mercaptoethyl)-1,4,4-trimethylpiperazinium bischloride (0.90 g, 3.44 mmol). After 1.25 h, diisopropylethylamine (0.1 mL, 0.57 mmol) was added and the stirring was continued for 2 h. A part of the acetonitrile was eliminated under reduced pressure and the resulting red mixture was chromatographed on PrepPak −500/C₁₈ (Water Associates) column with 25–75% acetonitrile in water as eluting solvent to give a yellowish powder (1.4 g) after lyophylization. The powder was solubilized in water and the solution was passed on a column (1.2×58 cm) of permutit S-1 Cl⁻ using water an eluting solvent. Lyophylization of the appropriate fractions gave 1.17 g of a powder that was repurified on a column of PrepPak −500/C₁₈. Lyophylization of the appropriate fractions gave a yellowish powder, 0.80 g (53%); ir (KBr)$v_{max}$: 3400 (br, OH), 1770 (C=O of the β-lactam), 1690 (C=O Of PNB ester), 1605 (aromatic), 1515 (NO₂), 1345 (NO₂) cm⁻¹; ¹Hmr (D₂O) δ:1.26 (d, J=6.3 Hz, 3H, CH₃CHOH), 3.39 (s, NCH₃), 4.00 (s), 5.37 (br, s, CH₂ of PNB), 7.60 (d, J=8.6 Hz, 2H, Ho of PNB), 8.20 (d, J=8.7 Hz, 2H, Hm of PNB); uv (H₂O)λ$_{max}$: 276 (ε12094), 306 (ε10752). Anal. calcd. for C₂₅H₃₆N₄O₆SCl₂.3H₂O: C 46.51, H 6.65, N 8.68, S 4.97, Cl 10.98; found: C 46.31, H 6.18, N 8.57, S 5.36, Cl 11.37.

D. (5R,6S)-3-[2-(1,4,4-trimethyl-1-piperazinium)ethylthio]-6-[1R-hydroxyethyl]-7-oxo-1-azabicyclo(3.2.0)hept-2-ene-2-carboxylate chloride

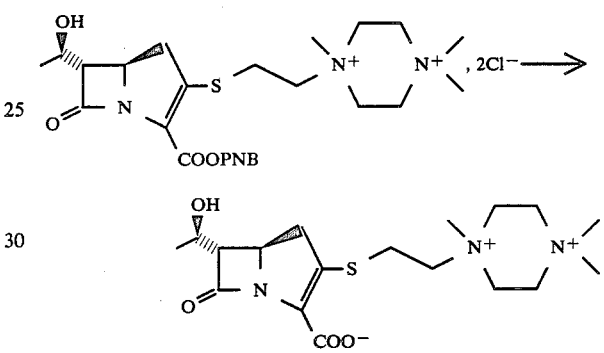

A mixture of (5R,6S)paranitrobenzyl 3-[2-(1,4,4-trimethyl-1-piperazinium)ethylthio]-6-[1R-hydroxyethyl]-7-oxo-1-azabicyclo(3.2.0)hept-2-ene-2-carboxylate bischloride (0.40 g, 0.68 mmol), phosphate buffer (30 mL, 0.05M, pH 7.0), tetrahydrofuran (10 mL), ether (30 mL) and 10% palladium on charcoal (0.40 g) was hydrogenated at 23° C. under 35 psi for 1 h. The two phases were separated. The organic phase was extracted with water (10 mL). The aqueous phases were filtered on a Celite pad, washed with ether (10 mL), concentrated under vacuum to 10 mL and chromatographed on PrePak-500/C₁₈ column (2.2×11 cm) with water as eluting solvent to give 70 mg (25%) after lyophylization; ir (KBr)$v_{max}$: 3400 (br, OH), 1755 (C=O of the β-lactam), 1585 (carboxylate) cm⁻¹; ¹Hmr (D₂O) δ: 1.24 (3H, d, J=6.3 Hz, CH₃CHOH), 3.36 (s, NCH₃), 3.98 (s); uv (H₂O) λ$_{max}$: 296 (ε7987); [α]$_D^{23}$35.9° (c, 0.30, H₂O), T½=9.8 h (measured at a concentration of 10⁻⁴M in phosphate buffer pH 7.4 at 36.8° C.).

We claim:
1. A compound of the formula

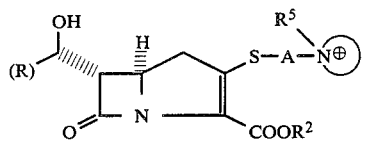

wherein A is cyclopentylene, cyclohexylene or C₂–C₆ alkylene optionally substituted by one or more C₁–C₄ alkyl groups; R² is hydrogen, an anionic charge or a conventional readily removable carboxyl protecting group, providing that when $R^2$ is hydrogen or a protecting group, there is also present a counter ion; and

represents

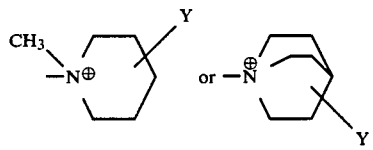

wherein Y is hydrogen, $C_1$–$C_6$ alkyl, hydroxy, —S$C_1$–$C_6$ alkyl, carboxyl, carbamoyl, chloro, bromo, iodo, fluoro or phenyl; or a pharmaceutically acceptable salt thereof.

2. A compound according to claim 1 wherein A is —$CH_2CH_2$—, —$CH_2CH_2CH_2$—,

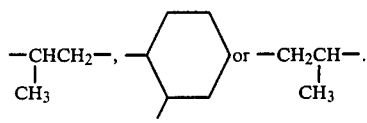

3. A compound of the formula

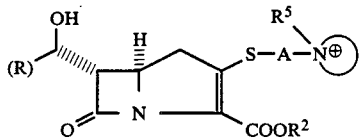

wherein A is cyclopentylene, cyclohexylene or $C_2$–$C_6$ alkylene optionally substituted by one or more $C_1$–$C_4$ alkyl groups; $R^2$ is hydrogen, an anionic charge or a conventional readily removable carboxyl protecting group, providing that when $R^2$ is hydrogen or a protecting group, there is also present a counter ion; and

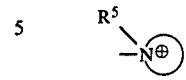

represents

or a pharmaceutically acceptable salt thereof.

4. A compound according to claim 3 wherein A is —$CH_2CH_2$—, $CH_2CH_2CH_2$—,

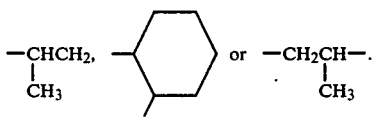

5. A compound of the formula

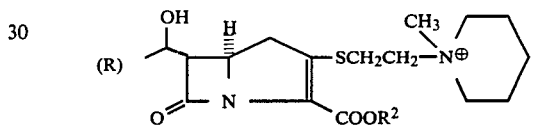

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

6. The compound according to claim 5 wherein $R^2$ is p-nitrobenzyl.

7. The compound according to claim 5 wherein $R^2$ is an anionic charge.

* * * * *